United States Patent [19]
Andersen et al.

[11] Patent Number: 5,756,449
[45] Date of Patent: May 26, 1998

[54] PEPTIDE T AND RELATED PEPTIDES IN THE TREATMENT OF INFLAMMATION, INCLUDING INFLAMMATORY BOWEL DISEASE

[75] Inventors: Anders Jorgen Andersen, Kokkedal, Denmark; Roger Aston, Wiltshire, England; Peter Louis Carlen, Ontario, Canada; Penelope Reed Doob, Ontario, Canada; Douglas Kevin MacFadden, Ontario, Canada; David James Phipps, Ontario, Canada; Deborah Rathjen; Fred Widmer, both of New South Wales, Australia

[73] Assignees: Peptide Technology Limited, Dee Why; Drug Royalty Corporation, New South Wales, both of Australia

[21] Appl. No.: 302,829
[22] PCT Filed: Mar. 29, 1993
[86] PCT No.: PCT/GB93/00649
§ 371 Date: Feb. 24, 1995
§ 102(e) Date: Feb. 24, 1995
[87] PCT Pub. No.: WO93/20102
PCT Pub. Date: Oct. 14, 1993

[30] Foreign Application Priority Data

May 14, 1992 [DK] Denmark .................... 0645/92

[51] Int. Cl.$^6$ .................................................. A61K 37/10
[52] U.S. Cl. .................................................. 514/8
[58] Field of Search .................................................. 514/8

[56] References Cited

FOREIGN PATENT DOCUMENTS 0249390  12/1987  European Pat. Off. .

Primary Examiner—Edward J. Cain
Attorney, Agent, or Firm—Banner & Witcoff, Ltd.

[57] ABSTRACT

A method of treating inflammatory bowel disease in patients in need of such treatment by administering an effective amount of: I-A-B-C-D-E-F-G-H-II (General Formula I), wherein A is Ala, Gly, Val, Ser, Thr or absent, B is Ala, Gly, Val, Ser, Thr, or absent, C is Ser, Thr or absent, D is Ser, Thr, Asn, Glu, Arg, Ile, Leu or absent, E is Ser, Thr, Asp or absent, F is Ser, Thr, Asp or absent, G is Tyr or absent, H is Thr, Arg, Gly, Met, Met(O), Cys, Thr, Gly or absent, and I is Cys or absent II is Cys, an amide group, substituted amid group, an ester group or absent. At least one of the amino acids optionally being substituted by a monomeric or polymeric carbohydrate or derivative thereof, such substitution being accomplished through hydroxyl and/or amino and/or amido groups of the amino acids, and wherein the peptide comprises at least 4 amino acid residues, and a pharmaceutically acceptable salt thereof.

18 Claims, 9 Drawing Sheets

PEPTIDE T AND RELATED PEPTIDES IN THE TREATMENT OF INFLAMMATION, INCLUDING INFLAMMATORY BOWEL DISEASE

This application is a 371 of PCT/GB93/00649, filed Mar. 29, 1993.

The present invention relates, broadly, to the treatment of prevention of inflammation, whether caused by bacteria, viruses and/or other infective agents, opportunistic infections (which may be consequent on an immunodepressed state, for example resulting from cancer or therapy, particularly cytotoxic drug therapy or radiotherapy) autoimmunity or otherwise. In particular embodiments, the invention relates to the prevention or treatment of neurodegenerative or demyelinating diseases such as HTLV-1-associated myelopathy (HAM), multiple sclerosis (MS) and symptoms or diseases in humans which are associated with chromatic immune activation. The invention also relates to pharmaceutical compositions useful in such treatment and/or prevention and to certain active peptides per se.

Septic shock is an illustration of a disease involving inflammation. Many of the clinical features of Gram-negative septic shock may be reproduced in animals by the administration of lipopolysaccharide (LPS). The administration of LPS to animals can prompt severe metabolic and physiological changes which can lead to death. Associated with the injection of LPS is the extensive production of tumour necrosis factor alpha (TNF-$\alpha$). Mice injected with recombinant human TNF develop piloerection of the hair (ruffling), diarrhoea and a withdrawn and unkempt appearance followed by death if sufficient amounts are given. Rats treated with TNF become hypotensive, tachypneic and die of sudden respiratory arrest (Tracey et al, 1986 *Science* 234, 470). Severe acidosis, marked haemoconcentration and biphasic changes in blood glucose concentration were also observed.

Histopathology of such rats revealed severe leukostatsis in the lungs, haemorraphic necrosis in the adrenals, pancreas and other organs and tubular necrosis of the kidneys. All of these changes were prevented if the animals were pretreated with a nuetralizing monoclonal antibody against TNF.

The massive accumulation of neutrophils in the lungs of TNF-treated animals reflects the activation of neutrophils by TNF. TNF causes neutrophil degranulation, respiratory burst as well as enhanced neutrophil antimicrobiocidal and antitumour activity (Klebanoff et al, 1986, *J. Immunol.* 136, 4220; Tsujimoto et al, 1986 *Biochem. Biophys. Res. Commun.* 137, 1094). Endothelial cells are also an important target for the expression of TNF toxicity. TNF diminishes the anticoagulant potential of the endothelium, inducing procoagulant activity and down-regulating the expression of thrombomodulin (Stern and Nawroth, 1986 *J. Exp. Med.* 163, 740).

TNF is a product of activated macrophages and is produced in response to infection and malignancy. It was first discovered in LPS-treated mice as a serum factor which caused the haemorraghic necrosis of transplanted tumours in murine models and was cytotoxic for tumour cells in culture (Carswell et al, 1975 *PNAS* 72, 3666; Helson et al, 1975, *Nature* 258, 731). Cachexia, which is characteristic of chronic exposure to TNF, is a common symptom of advanced malignancy and severe infection. It is characterised by abnormal lipid metabolism with hypertriglyceridaemia, abnormal protein and glucose metabolism and body wasting. Chronic administration of TNF and IL-1 in mice, rats and/or humans causes anorexia, weight loss and depletion of body lipid and protein within 7 to 10 days (Cerami et al., 1985, *Immunol, Lett.* 11, 173; Fong et al, 1989 *J. Exp. Med.* 170, 1627, Moldawer et al, *Am. J. Physiol.*, 254 G450–G456, 1988; Fong et al, *Am. J. Physiol.* 256 R659–R665 (1989); McCarthy et al, *Am. J. Clin, Nutr.* 42 1179–1182, 1982). TNF levels have been measured in patients with cancer and chronic disease associated with cachexia. The results are inconclusive since large differences in TNF levels have been reported. These may have been explicable by the short half-life of TNF (6 minutes), differences in TNF serum binding protein or true differences in TNF levels in chronic disease states.

TNF-$\alpha$ and IL-1, with their common functional activities such as pyrogenicity, somnogenicity and being mediators of inflammation, have been implicated in the pathology of other diseases associated with chronic inflammation, apart from toxic shock and cancer-related cachexia. TNF has been detected in synovial fluid in patients with both rheumatoid and reactive arthritis and in the serum of patients with rheumatoid arthritis (Saxne et al, 1988, *Arthrit, Rheumat.* 31, 1041). Raised levels of TNF have been detected in renal transplant patients during acute rejection episodes (Maury and Teppo 1987, *J. Exp. Med.* 166, 1132). In animals, TNF has been shown to be involved in the pathogenesis of graft-versus-host disease in skin and gut following allogenic marrow transplantation.

Administration of a rabbit anti-murine TNF antibody was shown to prevent the histological changes associated with graft-versus-host disease and to reduce mortality (Piquet et al, 1987, *J. Exp. Med.* 166, 1220). TNF has also been shown to contribute significantly to the pathology of malaria (Clark et al, 1987, *Am. J. Pathol.* 129, 192–199). Further, elevated serum levels of TNF have been reported in malaria patients (Scuderi et al, 1986, *Lancet* 2, 1364–1365.

Multiple sclerosis (MS) is generally considered by many authorities to be a chronic inflammatory disease.

Both MS and HTLV-1 associated myelopathy (HAM) affect the central and the peripheral nervous systems and both may present clinically as a myelopathy affecting both the spinal nerves and the spinal myelinated nerve fibres.

Multiple sclerosis (MS) is a chronic demyelinating disease of the central nervous system and is the commonest chronic neurological disease of young adults. The incidence of MS and its pattern of distribution have been unchanged for decades. The disease remains essentially untreatable.

MS has always been regarded as a disease of the temperature zones and has a prevalence in the northern United States, Canada and Europe of 1:1000. The disease has a gender predilection of 1.5:1 (female:male).

MS usually affects multiple areas of white matter in the central nervous system (CNS), most frequently, the periventricular white matter, brainstem, spinal cord and the optic nerves. The primary process destroys myelin sheaths and eventually kills oligodendrocytes creating the characteristic plaque of MS.

The early development of the plaque is characterised by the development of perivascular inflammation followed by the migration of lympnocytes, plasma cells and macrophages into the lesion. This is followed by astrocyte gliosis and the attempts of remyelination by oligodendrocytes. The plaque is surrounded by lymphocytes.

Although the aetiology of MS is still unknown, the focus of research efforts that have led to plausible hypotheses have been those of immune dysregulation including autoimmunity and genetic predisposition, both of which may play a role in the actual development of disease.

Multiple immunological abnormalities are reproducibly found in patients in the acute stage of the disease. The synthesis of immunoglobulins, although normal in the periphery, is increased in the central nervous system and the antibodies produced have a characteristic banding pattern. The antigenic specificity of these antibodies is not known and it is unclear whether they have a role to play in the progression of disease.

Various stressors known to activate the immune system such as viral infection or surgery can also produce an exacerbation of MS. Other activators such as γ-interferon produce similar effects when administered. In addition, immunosuppressive anti-inflammatory thereby with corticosteroids for example, can produce modest remission or at least palliation for short periods of time, although this therapy is controversial.

Lymphocyte reactivity against two neuronal antigens, myelin basic protein and proteolipid has been demonstrated. Although not proven, this activity would form the basis for an autoimmune response against neuronal tissue.

The discovery of the neurotropic capacity of HTLV-1 in patients from Martinique with tropical spastic paraparesis (TSP) and in Japan with chronic myelopathy, has demonstrated HTLV-1 as the common aetiologic agent of these diseases. It has subsequently been shown that the neurologic manifestations of HTLV-1 infection are the same despite the varied geographic regions in which they are described.

The neurological signs of this chronic retroviral infection including slowly progressive spastic paraparesis with spastic bladder and minimal sensory deficits result from involvement of the pyramidal tracts in a bilateral and symmetrical fashion predominantly at the thoracic level of the spinal cord.

The peripheral nervous system has been shown to be involved, resulting in slowing of nerve conduction velocities in the lower limbs. Systemic manifestations of HTLV-1 in patients with HTLV-1 myelopathy have been described and include inflammatory involvement of the lungs, skin, eyes and striated muscle producing a myositis. In addition, patients experience profound fatigue similar to MS. The clinical manifestations of the disease are every similar to MS and are frequently confused with the latter.

There are at least four possible pathogenetic mechanisms whereby HTLV-I can involve the CNS to produce HAM. These may include a slow virus infection, a cell-mediated immune response and a predominantly humoral immune mediated mechanism and the development of an autoimmune phenomenon. The slowly progressive course supports the hypothesis of a slow virus infection. The finding of peri-vascular cuffing in post-mortem specimens as well as transiently favourable response to steroids supports the hypothesis that an inflammatory immune reaction, probably a result of viral infection, is responsible for the development of HAM.

These two diseases have many similarities and dissimilarities, both clinical and neurological. Both diseases are a form of demyelinating disease whereby the myelin sheath of the nervous system is destroyed by one of many mechanisms common to both diseases and also peculiar to either of the diseases. MS is a multi-faceted disease in that it can be both a central nervous system disease which can include a myelopathy. Conversely, HTLV-1-associated myelopathy is predominantly a myelopathy which can occasionally demonstrate central nervous system effects. Furthermore, MS can affect the peripheral nervous system in ways that are common in HTLV-1.

Myelopath, as already mentioned in being a disorder of the spinal cord, can have many different aetiologies from MS and HAM. Various forms of myelopath, most of which are mediated by inflammation, include the following:

neurosyphillis;

$B_{12}$ or folate deficiency;

sarcoidosis;

transverse myelitis;

arachnoiditis;

cervical spondylitis;

motor neuron disease;

neurofibromatosis;

spinal cord compression from tumour, disc or arthritis;

lupus erythematosus of the spinal cord; and viral encephalomyelitis.

Chronic inflammation or, as more commonly known, chronic immune system activation occurs in response to persistent antigen whose origin may be exogenous or endogenous or may result from an autoimmune state. Such chronic inflammation results in local tissue destruction and depending upon the type of inflammation can result in systemic effects due to the sustained production of inflammatory mediators. Such inflammatory mediators include the cytokines which are soluble mediators produced by activated lymphocytes and macrophages and effect cellular communication and physiological response. Chronic immune activation can occur as a result of infectious diseases, such as chronic fatigue syndrome or toxic shock syndrome or through autoimmune mechanisms resulting in such conditions as rheumatoid arthritis, inflammatory bowel disease and variants such as graft versus host interactions.

The immune response to antigen may be divided into four overlapping phases: initiation (antigen presentation), amplification (cell activation), effector and regulation (Roitt et al. "Immunology", Gower Medical Publ. London, EK. 1989; "Basic and Clinical Immunology", Stites et al. Eds. Appleton and Lange, Norwalk, Conn. 1991). Briefly antigen is phagocytosed by antigen presenting cells (APC) which must express major histocompatibility (MHC) Class II molecules on their surface. In this respect, cells of the macrophage/ monocyte lineage (CD4 positive) and B cells (CD4 negative) may act as APC. Following phagocytosis, antigen is processed intracytoplasmically and expressed on the surface as antigenic fragments in association with MHC-II molecules. The combination of antigen/MHC-II induces the activation of T helper cells (CD4 positive) in an antigen-specific manner and primes them to receive a second antigen non-specific activating signal. Activated T helper cells then induce the activation of effector T cells (cytotoxic lymphocytes, CD4 negative) and B cells which produce antibody. Effector cells and molecules facilitate the elimination of antigen by a variety of antigen specific and non-specific mechanisms that may result in host tissue damage if effector mechanisms are expressed inappropriately by deposition of antigen or immune complexes on host tissues, responding to self-antigens or as a result of a prolonged (chronic) immune response. Regulation of the immune response via removal of antigen, active suppression or idiotypic regulation limits the normal immune response to a duration of one to three weeks.

Chronic fatigue syndrome (CFS) or chronic fatigue immune dysfunction syndrome (DeFritas et al, *Proc. Natl. Acad. Sci.* 88, 2922–2926 (1991)) is a condition of unknown aetiology characterized by a diverse set of signs and symptoms including severe fatigue, post-exertional malaise, headaches, night sweats, myalgia, ataxia, low grade fever and lymphadenopathy (CDWR 1–3: Joncas J. H., Welcome and Introduction in: *Proceedings of a Workshop: chronic Fatigue Syndrome*, Can. Dis. Weekly Report vol. 17S1E, January 1991 pages 1–3). Although the origin of CFS is unknown its symptoms are consistent with over-production of cytokines (Landay et al, Lancet 338 707–712 (1991)). CFS-like symptoms have been observed following the therapeutic administration of interferons (IFNs) (Lloyd et al, Med. J. Aust. 151 122–124 (1989); Lever et al, Lancet 2 101 (1988); Mowbray et al, Br. Med. Bull. 47 886–894 (1991)) and interleukin-2 (IL-2) (Cheney et al, Annal. Intern. Med. 110 321 (1989)). In a trial of IFN-α in patients with CFS, the drug exacerbated the condition further supporting a cytokine-mediated pathogenesis (McBride et al, Br. Med. Bull. 47 895–907 (1991)). The serum and cerebrospinal fluid of patients with CFS has been shown to contain increased levels of IL-2, IFN and IL-1 (Wallace et al, Arth. Rheum. 32 1334–1335 (1989); Shepperd The Practitioner 233 41–46 (1989)) as well as IL-6 (Chao et al, J. Infect. Dis. 162 1412 (1990)). In addition neopterin, a marker of macrophage activation (Chao et al, J. Infect. Dis. 162 1412 (1990)) and the IFN-associated enzyme 2'-5'-oligoadenylate synthetase (Klimas et al, J. Clin. Microbiol. 28 1403–1410 (1990)) are both increased in CFS as are other markers of macrophage activation such as ICAM-1 and LFA-1 (Gupta et al, Scan. J. Immunol. 33 319–327 (1991)). CFS-associated anergy to skin test antigens (Johnson et al, FASEB J. 5 2706–2712 (1991)), reduction in lymphocyte response to mitogens (Klimas et al, J. Clin. Microbiol. 28 1403–1410 (1990)) and soluble antigen (Gupta et al, Scand. J. Immunol. 33 319–327 (1991)) are consistent with macrophage dysfunction (Prieto et al, Scand. J. Immunol. 30 13–20 (1989)) and may be explained by an autocrine exhaustion of immunocompetent cells by chronic activation resulting in immunodysregulation (CDWR 1–3: Joncas J. H., Welcome and Introduction in: Proceedings of a Workshop: Chronic p Fatigue Syndrome, Can. Dis. Weekly Report vol. 17S1E, January 1991, pages 49–50).

CFS and the acquired immune deficiency syndrome (AIDS, see below) share many symptoms (Miller et al, Neurology 41 1603–1607 (1991) and laboratory findings (Gupta et al, Scand. J. Immunol. 33 319–327 (1991)); and one study has demonstrated an association between infection with the HIV related retrovirus HTLV-II and CFS (Gupta et al, Scand. J. Immunol. 33 319–327 (1991).

There is no accepted drug therapy for CFS. There have been anecdotal reports of beneficial effects following administration of amantidine, monoamine oxidase inhibitors (ie phenelzine), fatty acid supplements (McBride et al, Br. Med. Bull. 47 895–906 (1991) and 5-hydroxytryptophan (Caruso et al, J. Int. Med. Res. 18 201–209 (1990)) among others, but controlled studies have not demonstrated efficacy.

Toxic shock syndrome (TSS) is produced by a *Staphylococcus aureus* enterotoxin. Toxic shock syndrome toxin-1 (TSST-1). TSST-1 belongs to a family of staphylococcal enterotoxins which are mitogenic for T cells expressing particular Vβ genes (Kappler et al, Science 244 811–813 (1989)). As a result of their non-specific mitogenicity, staphylococcal enterotoxins can induce the proliferation of up to 20% of T-cells and have been called "superantigens" (Johnson et al, Sci. Am. 266 92–101 (1992)). Macrophages are required to present TSST-1 to T-cells (Poindexter et al, J. Infect. Dis. 151 65–72 (1985)); however, like other staphylococcal enterotoxins, TSST-1 does not require antigen processing for T-cell activation (Pontzer et al, Proc. Natl. Acad. 88 125–128 (1991)). The native molecule binds outside the antigen binding cleft of MHC Class II molecules to a non-polymorphic region of the β chain (Fraser Nature 339 221–223 (1989); Johnson et al, FASEB J. 5 2706–2712 (1991)).

The symptoms of TSS (such as fever, rash, hypotension, nausea, vomiting and diarrhoea) are consistent with over-activation of the immune system (Johnson et al, Sci. Am. 266 92–101 (1992) and over-production of cytokines (Ikejima et al, J. Clin. Invest. 73 1312–1320 (1984); Micussan et al, Immunology 58 203–208 (1986)). These symptoms have been reproduced in animal models by the administration of tumour necrosis factor (TNF) (Miethke et al, J. Exp. Med. 175 91–98 (1992)). Massive immune activation of this nature could lead to exhaustion of immunocompetent cells and may explain the immunosuppression associated with enterotoxin shock (Langford et al, Infect. Immun. 22 62–68 (1978)) and in vitro enterotoxin-induced T-cell anergy (O'Hehnir et al, Immunol. Lett. 30 165–170 (1991)).

Therapy of TSS involves immediate replacement of lost fluid to counter hypovolaemia. If the patient fails to respond to anti-staphylococcal antibiotics then steroid therapy (ie methylprednisone) may be required for those in severe shock (Todd, Drugs 39 856–861 (1990)).

Rheumatoid arthritis (Marrow et al, "Autoimmune Rheumatic Disease", Blackwell Scientific Publ., Oxford, UK, Chapter 4, pp 148–207 (1987)) is a disease characterised by chronic inflammation and erosion of joints that may affect up to 3% of the population, including children. Symptoms of rheumatoid arthritis include morning stiffness, swelling and pain upon motion in at least one joint and joint swelling. Non-specific symptoms including lethargy, anorexia and weakness as well as fever and lymphadenopathy (characteristic of immune activation) may antedate joint involvement. Extra-articular manifestations of rheumatoid arthritis include vasculitis, cataracts, uveitis, interstitial fibrosis, pericarditis and myocarditis, peripheral neurophathy, myeloid deposits, chronic anaemia and subcutaneous and pulmonary nodules.

Genetic factors and infectious agents including bacteria, fungi, mycoplasmas and viruses have been associated with the development of rheumatoid arthritis. Mild rheumatoid arthritis may be treated with non-steroidal anti-inflammatory drugs while severe cases require systemic corticosteroids, anti-metabolites or cytotoxic agents. Experimentally, anti-CD4 monoclonal antibodies have been used to treat rheumatoid arthritis (Horneff et al, Cytokine 3 266–267 (1991); Horneff et al, Arth. Rheum. 34 129–140 (1991) and Shoenfeld et al, Clin. Exp. Rheum. 9 663–673 (1991)).

Inflammatory bowel disease (IBD) is a chronic inflammatory condition that fulfils some of the criteria of an autoimmune disease (Snook, Gut 31 961–963 (1990)). Inflammation and tissue damage involves the recruitment and activation of neutrophils, macrophages and lymphocytes (MacDermott et al, Adv. Immunol. 42 285–328 (1988)) which generate cytokines and proinflammatory molecules such as prostaglandins and leukotrienes (MacDermott, Mt. Sinai J. Med. 57 273–278 (1990)). As a result of chronic activation of immunocompetent cells, IL-1, IL-6 (Starter, Immunol. Res. 10 465–471 (1991); Fiocchi, Immunol. Res. 19 239–246 (1991)) and TNF-α (MacDermott, Mt. Sinai J. Med. 57 273–278 (1990)) are all elevated in IBD patients.

Drugs used to treat IBD include anti-inflammatory agents such as sulphasalazine (5-ASA), corticosteroids, cyclosporin A and azathioprine (Hanauer, Scan. J. Gastroenterol. 25 (Supp. 175) 97–106 (1990); Pepperscorn, Annal. Intern. Med. 112 50–60 (1990)). Experimentally, anti-CD4 monoclonal antibodies have been used to successfully treat ulcerative colitis (Emmrich et al, Lancet 338 570–571 (1991)).

While a host may react against a genetically incompatible graft producing a host-versus-graft response, an immunocompetent graft (such as bone marrow or intestinal tissue) may react against the host resulting in graft-versus-host disease. These reactions are mediated by allogenic responses directed against a foreign MHC molecule and are mimicked in vitro by the mixed lymphoctye reaction (MLR). Graft/ host interactions result in chronic inflammation surrounding the grafted tissue with an increase in markers of immune activation such as are seen in AIDS (Grant, *Immunol. Today* 12 171–172 (1991). Treatment of the graft/host interactions currently include either azathioprine, cyclosporin A or methylprednisone and, more recently, rapamycin (Stepkowski et al, *Transplantation* 53 258–264 (1992); Huber et al, *Bibliotheca Cardiologica*. 43 103–110 (1988)). Monoclonal antibodies specific for CD3 (Wissing et al, *Clin Exp. Immunol.* 83 333–337 (1991) and CD4 (Reinke et al, *Lancet* 338 702–703 (1991) have been used experimentally to inhibit graft/host reactions. The present invention deals with the identification of a group of peptides that alleviates the inflammatory response in number of diseases. These include: autoimmune disease; organ transplantation; neoplasia; viral, bacterial, fungal or other infections; and, in particular, any disease wherein infection can manifest in an opportunistic fashion, eg during cytotoxic or radiation therapy or in any situation where an immunodepressed state exists. Peptides useful in the present invention do not necessarily interfere directly with the pathogenic mechanisms of the disease-causing component. As will be described below in the experimental data, the mechanism whereby these peptides can alleviate the symptoms of these diseases in dependent on their capability of modulating the production and effect of cytokines produced by activated cells of the immune system. The modulation of cytokines may not be limited to TNF but may also be valid for a whole range of interleukins, for example from interleukin-1 to interleukin-10. The data presented are at present not direct evidence, but rather a powerful indirect model. Thus, the model uses one of the most powerful inflammatory compounds known, LPS, which binds to receptors on neutrophils, monocytes and macrophages; these cells consequently become activated and start production of IL-1 and TNF, among other cytokines, thus starting the inflammatory cascade. One parameter used to measure this effect of LPS is the concentration of blood glucose, which normally decreases on exposure to TNF or LPS. From what is known in the literature about the mechanism of Peptide T at a cellular level, it is therefore highly surprising that Peptide T and its analogues are able significantly to reduce the negative effects of LPS. LPS normally combines with LPS-Binding Protein (LBP) and exerts its dramatic effect through the CD14 receptor. In the literature up to date, the peptides useful in this invention have only been connected to the CD4 receptor, which is not believed to be involved in the primary inflammatory response associated with cytokines, such as TNF, or LPS.

More specifically, it has been discovered that a particular group of peptides, particularly those within the group having at least 5 amino acid residues, are very effective agents useful in the treatment, inter alia, MS and HAM, and are likely to be useful in treating other myelopathies, most of which have similar disease mechanisms.

From the above discussion, it is apparent that many symptoms and diseases are associated with chronic inflammation; however, several of these diseases appear to involve different mechanisms. It is therefore important that particular compounds have been found which are useful in treating symptoms and diseases associated with chronic inflammation where it appears that these compounds interact in some manner with CD4 receptors of immune system cells. The compound relate, as indicated above, to Peptide T and its various derivatives. It was originally thought that such compounds had no effect on the immune system other than being very useful in blocking attachment of HIV virus to CD4 receptor cells (Ruff et al, IV International Conference on AIDS, Stockholm June 1988).

Originally, many of the peptides useful in the invention were described as being effective in the prevention of infection and replication of HIV in vitro; see EP-A-0249390, EP-A-0249394 and WO-A-8809338, all of which are incorporated by reference to the maximum extent allowed by law, as are all other documents referred to in this specification. All compounds disclosed in these specifications are useful for the present invention. The original peptide has its basic point of origin in the octapeptide Ala-Ser-Thr-Thr-Thr-Asn-Tyr-Thr. It is called Peptide T because 50% of the amino acid residues are threonines. This peptide has been identified from a subregion of the human immune deficiency virus (HIV) external glycoprotein molecule gp120, which is responsible for binding to any cell carrying the CD4 molecule and, in particular, helper lymphocytes, microglial cells in the CNS, monocytes and dendritic cells. Binding occurs via specific attachment of gp120to the CD4 molecule. Treating individuals infected with HIV with this peptide and its derivatives, which are described below, consequently has the effect of potentially inhibiting binding of the whole virus or the neurotoxic gp120 molecule to the cell receptor CD4. In this way, the cell is protected from infection, and so the virus, being unable to replicate, is destroyed by the immune defence.

According to a first aspect of the present invention, there is provided the use of a linear or cyclic peptide of General Formula 1;

I-A-B-C-D-E-F-G-H-II        (General Formula 1) (SEQ ID NO:1)

wherein A is Ala, Gly, Val, Ser, Thr or absent,

B is Ala, Gly, Val, Ser, Thr or absent

C is Ser, Thr or absent,

D is Ser, Thr, Asn, Glu, Arg, Ile, Leu or absent,

E is Ser, Thr, Asp or absent,

F is Thr, Ser, Asn, Arg, Gln, Lys, Trp or absent,

G is Tyr or absent,

H is Thr, Arg, Gly, Met, MET(O), Cys, Thr, Gly or absent,

I is Cys or absent,

II is Cys or absent, at least one of the amino acids optionally being substituted by a monomeric or polymeric carbohydrate or derivative thereof, such substitution being accomplished through hydroxyl and/or amino and/or amido groups of the amino acids.

and wherein the peptide comprises at least four amino acid residues, or a pharmaceutically acceptable salt thereof, in the manufacture of a medicament for treating or preventing inflammation.

Each of the amino acids referred to in General Formula 1 may be in the L- or D- stereoisomeric configuration and candidates for H may be esterified or amidated. The peptide comprises at least 4 amino acids.

Tetra-, penta-, hexa-, hepta-, octa- and nona-peptides useful in the invention are all of the peptides chosen from the sequence;

I-A-B-C-D-E-F-G-H-II by deleting residues, for example, one at a time, from either the carboxyl or amino terminal, or from within the sequence.

It is appreciated that peptides having the core sequence of Thr-Thr-Asn-Tyr-Thr- may have at both ends additional amino acid residues, some of which are represented by General Formula 2:

X-Ser-Thr-Thr-Thr-Asn-Tyr-Y(General Formula 2) (SEQ ID NO:2)

wherein X is an amino acid terminal residue selected from Ala and D-Ala and Y is a carboxy terminal residue selected from Thr and Thr-amide.

A particular preferred peptide of the group of peptides has the aforementioned core sequence of -Thr-Thr-Asn-Tyr-Thr-. These peptides of the above General Formula 2, and in particular a variant Peptide T of the formula -Ser-Thr-Thr-Thr-Asn-Tyr-, were found to be very useful in inhibiting binding of the human immunodeficiency virus (HIV) to human cells by blocking receptor sites on the cell surfaces. The term Peptide T is used throughout the specification to reference, unless the context otherwise requires, peptides of General Formula 2 which all include the core peptide sequence. It is therefore intended that Peptide T encompass all of the compounds of General Formula 2 where it is understood that all such compounds are variants of the normally understood octapeptide T, also referred to as prototype Peptide T, of the particular formula D-Ala-Ser-Thr-Thr-Thr-Thr-Asn-Tyr-Thr-amide (SEQ ID NO:3).

The invention may be useful in both clinical (human) and veterinary medicine. The invention therefore has application in a method for treating or preventing inflammation, the method comprising administering to a human or other animal subject, for example on a repeated basis, a peptide of General Formula 1. The peptide will generally be administered in an effective, non-toxic amount or in such an amount that strikes an acceptable balance between efficacy and toxicity, having regard to the circumstances of the case.

Preferred peptides useful in the invention have, as their active portion, an amino acid sequence of the formula:

-Thr-Thr-Asn-Tyr-Thr- (SEQ ID NO:4)

These peptides, while being useful for all prophylactic and therapeutic utilities within the invention, are particularly preferred for the prevention or treatment of MS and HAM and for the prevention or treatment of symptoms or diseases, in humans or other animals, associated with chronic immune activation, chronic inflammation and chronic autoimmune disease.

Most preferred peptides useful in the invention, then, are the following:

1. D-Ala-Ser-Thr-Thr-Thr-Asn-Tyr-Thr-NH$_2$ (prototype Peptide T) (SEQ ID NO:3)
2. Ala-Ser-Thr-Thr-Thr-Asn-Tyr-Thr (SEQ ID NO:5)
3. D-Ala-Ser-Thr-Thr-Thr-Asn-Tyr-Thr (SEQ ID NO:3)
4. D-Ala-Ala-Ser-Ser-Ser-Asn-Tyr-Met (SEQ ID NO:6)
5. Thr-Asp-Asn-Tyr-Thr (SEQ ID NO:7)
6. Thr-Thr-Ser-Tyr-Thr (SEQ ID NO:8)
7. Thr-Thr-Asn-Tyr-Thr (SEQ ID NO:4)
8. D-Thr-Thr-Tyr-D-Thr (SEQ ID NO:9)
9. D-Ala-Ser-D-Thr-Thr-D-Thr-Asn-Tyr-D-Thr-NH$_2$ (SEQ ID NO:10)
10. D-Ser-Ser-D-Thr-Thr-D-Thr-Thr-Tyr-D-Thr-NH$_2$ (SEQ ID NO:11)

Quite often it may be an advantage to have the amino terminal amino acid as a D-stereoisomeric, to protect the molecule from degradation from aminopeptidases; alternatively or additionally, the carboxy terminal amino acid may be an amino acid amide to protect the molecule from degradation from carboxypeptidases. In this connection, compounds 5, 6 and 7, listed above, include analogues with D-Thr as the amino terminal residue and/or an amide derivative at the carboxy terminal.

Furthermore, it should be understood that one more of the amino acids in the peptides may be substituted N-alkyl (eg ($C_1$–$C_4$) alkyl) amino acids instead of primary amino acids; examples include methyl and ethyl. The hydroxyl group side chains of one or more of the amino acids (Ser, Thr, Tyr) may be derivatised into an ether or ester group. Any (optionally substituted) alkyl ester or ether may be formed, such as ($C_1$–$C_4$) alkyl, aryl or aryl ($C_1$–$C_4$) alkyl esters, ethers, thioesters and thioethers, for example phenylester, benzylether or thiophenol ethylester. The presently preferred ethers are methyl, ethyl and propyl ethers and presently preferred esters are methyl, ethyl and propyl esters.

The hydroxyl side chains of the amino acids Ser, Thr and/or Tyr and the amido groups of the amino acids Asn' and/or Gln may be substituted with different carbohydrates or derivatives of carbohydrates. Carbohydrate derivatives may be as discussed above.

Linear peptides useful in this invention may be prepared by any suitable process, such as conventional solid phase peptide synthetic techniques; see "Solid Phase Peptide Synthetic Techniques", 2nd ed, J. M. Stewart, J. D. Young, Pierce Chemical Company, 1984, ISBN: 0-935940-03-0. A frequently used solid phase method is the Merrifield technique. Another possibility is solution phase techniques. The preferred peptide, prototype Peptide T, is readily obtainable from Carlbiotech A/S, Copenhagen, Denmark.

Cyclic peptides useful in the invention may be prepared by known techniques, such as, for example, described in Y. Hamada in *Tetrahdron Letters*, 26 5155 (1985). Cyclic peptides may be established in the form of a disulphide bridge between two Cys residues and/or by reacting the carboxy terminal amino acid residue with the amino terminal residue and/or by reacting the amino terminal residue with for example the γ-carboxyl group of Glu, when Glu is at position D.

Carbohydrate derivatives may be prepared by methods known in the art.

Certain peptide derivatives useful in the invention are new and themselves form another aspect of the invention according to which there is provided a linear or cyclic peptide of General Formula 1;

I-A-B-C-D-E-F-G-H-II (General Formula 1)

wherein A is Ala, Gly, Val, Ser, Thr or absent,

B is Ala, Gly, Val, Ser, Thr or absent,

C is Ser, Thr or absent,

D is Ser, Thr, Asn, Glu, Arg, Ile, Leu or absent,

E is Ser, Thr, Asp or absent,

F is Thr, Ser, Asn, Gln, Lys, Trp or absent,

G is Tyr or absent,

H is Thr, Arg, Gly, Met, Met(O), Cys, Thr, Gly or absent,

I is Cys or absent,

II is Cys or absent, at least one of the amino acids being substituted by a monomeric or polymeric carbohydrate or derivative thereof, such substitution being accomplished through hydroxyl and/ or amino and/or amido groups of the amino acids.

and wherein the peptides comprises at least four amino acid residues.

except for glycosylated proptotype Peptide T, or a pharmaceutically acceptable salt thereof.

Glycosylated Peptide T is disclosed in Urge et al., *Biochem. Biophys. Res. Comms.* 184(2) 1125–1132 (1992), published 30 Apr. 1992, but the utility of the present invention is neither disclosed nor suggested.

Preferred features of this aspect of the invention are as for the first aspect.

Peptides useful in the invention may be administered as a composition in conjunction with a pharmaceutically acceptable carrier.

In this way the peptides can be used in pharmaceutical compositions and compositions of matter for treating and preventing any disease or condition caused by an organism, compound or immune dysfunction that results in an inflammatory reaction of the immune system.

The peptides or peptide formulations may be used alone or in combination with an other pharamceutically active compound, such as an anti-infective agent, for example an antibiotic and/or antiviral agent and/or antifungal agent, or another pharmaceutically active compound, such as an anti-neoplstic agent.

The peptides may be administered orally, bucally, parenterally, topically, rectally, vaginally, by intranasal inhalation spray, by intrapulmonary inhalation or in other ways.

In particular, the peptides according to the invention may be formulated for topical use, for inhalation with spray or powder, for injection (for example subcutaneous, intramuscular, intravenous, intra-articular or intr-cisternal injection), for infusion or for oral administration and may be presented in unit dose form in ampoules or tablets or in multidose vials or other containers with an added preservative. The compositions may take such forms as suspensions, solutions, or emulsions or gels in oily or aqueous vehicles, and may contain formulatory agents such as suspending, stabilising and/or dispersing agents. Alternatively, the active ingredient may be in powder and/or lyophilised form for direct administration or for constitution with a suitable vehicle (eg sterile, pyrogen-free water, normal saline or 5% dextrose) before use. The pharmaceutical compositions containing peptide(s) may also contain other active ingredients such as antimicrobial agents, or preservatives. The compositions may contain from 0.001–99% (w/v or, preferably, w/w, of the active material. Peptide T obtainable from Carlbiotech A/S is usually formulated and packaged in a sterile manner in 5% dextrose solution in multi-dose vials. It will be appreciated that the peptide may be packaged in other carriers, such as saline. Preferably, the concentration of peptide in each dose is in the order of 8.5 mg/ml for subcutaneous injection in one ml doses.

The compositions are administered in therapeutically or prophylactic effective doses, ie 0.05–10000 mg of peptide per day, in particular 5–1000 mg per day. Very large doses may be used as the peptide according to the invention is non-toxic. However, normally this is not required. The dose administered daily of course depends on the degree of inflammation and inflammatory response.

For administration by injection or infusion of the composition, the daily dosage, as employed for treatment of adults of approximately 70 kg of body weight, will often range from 0.2 mg to 20 mg of active material which may be administered in the form of 1 to 4 doses over each day, such dosage ranges depending upon the route of administration and the condition of the patient.

Compositions as described above maybe prepared by mixing or otherwise bringing into associated the ingredients.

The invention may be useful in the prevention or treatment of illness or medical conditions, particularly those involving inflammation, such as:

Viral, bacterial or drug-induced hepatitis or meningitis;

Rheumatoid, psoriatic, reactive, or osteoarthritisor other arthritides;

Sepsis/septic shock;

Dermal inflammation;

ARDS (adult respiratory distress syndrome)

Graft rejection;

Inflammation secondary to the chemotherapy or radiotherapy of neoplastic disease.

The invention finds particular use in the prevention or treatment of MS, HAM and other inflammatory myelopathies (particularly those previously specifically mentioned) and/or symptoms or diseases in humans which are associated with chronic immune activation. More particularly, the invention is useful in treating chronic fatigue syndrome, toxic shock syndrome associated with *Staphylococcus aureus* infection, arthritis, inflammatory bowel disease and host-versus-graft response in transplant patients. Such efficacious results in the use of the above compounds is thought to be due, without being limited to any particular theory, to the immunosuppressive activities of these compounds in chronic inflammatory states.

In order to provide a guideline for the administration of and insight into the use of the peptides according to the invention, particularly the treatment of MS, myelopathies such as HAM and chronic inflammation, and the formulation of the compositions, the following is offered as a guide based on the extensive work already conducted in the use of peptide T for treating HIV infection.

Peptide T is an octapeptide homologous to a region of gp120, an HIV envelope glycoprotein, and to human vasoactive intestinal peptide (VIP). It was originally developed by Perc et al (EP-A-0249394), to block the binding of gp120 (an HIV envelope glycoprotein) and thus also block binding of HIV to CD4, the specific membrane-bound vial receptor, thereby blocking internalisation of the virus into the cell—a process necessary for viral replication. The CD4 molecule necessary for the entry of HIV into cells has been localized on the surface of lymphocytes, macrophages, microglial cells, neurons and numerous other cells. Binding of HIV to the CD4 receptor has been demonstrated to effect viral entry; and binding of free (non-viral related) gp120 has resulted in neuronal toxicity in both in vitro and in vivo studies.

The efficacy of Peptide T in reversing signs of HIV-induced dementia has been demonstrated in both the peptide T Phase I clinical trial at the University of southern California in Los Angeles and in the Phase II clinical trial at the Fenway Clinic in Boston. Both studies have demonstrated improvement in the HIV-induced neurocognitive impairment in patients with AIDS.

To date, the Peptide T/gp120/VIP homology has been used to explain at least two possible mechanisms of action of Peptide T. Firstly, that is competitively binds to CD4 (the known receptor for HIV) on human cell surfaces and competes with both HIV and gp120 for binding sites.

The binding of Peptide T and its analogues of General Formula 1, or more particularly General Formula 2, to CD4 could produce a blocking effect to prevent the binding of any other molecule capable of binding to that receptor; alternatively, or in addition, the binding of Peptide T to CD4 could induce a reaction similar to that caused by the endogenous ligand.

CD4 is the differentiation antigen that defines the T lymphocyte subgroup of helper/inducer cells, but it is also present on a wide variety of cells including neurons, activated macrophages and B cells. CD4 is the predominant receptor for HIV and was originally thought to be necessary for cellular infection. Using the monoclonal antibody OKT4, Pert et al (*Proc. Natl. Sci. USA* 83 9254–9258 (1986); Pert et al (*Clin. Neuropharmacol.* 9(4S198 (1986)) demonstrated the presence of this antigen throughout the human CNS and showed that it is present in highest concentration in the dentate gyrus, hippocampus, amygdala and deep cortex. This distribution was found to be similar to that found in other higher mammals. Peptide T and similar analogues were found to inhibit the binding of radiolabelled gp120 to rat hippocampal membranes and to do so in 0.1 nM concentrations.

Using Peptides T and the same analogues, Pert et al. (*Proc. Natl. Sci. USA* 83 9254–9258 (1986); Pert et al (*Clin. Neuropharmacol.* 9(4) S198 (1986)) were able to demonstrate a reduction in the detectable levels of HIV reverse transcriptase when these peptides were present in an assay of HIV infectivity. A ninefold reduction of reverse transcriptase took place at 100 nM concentrations of Peptide T.

Since gp120 is not identical in all isolated strains of HIV, a comparison was made with nine different HIV isolates Pert et al. (*Clin. Neuropharmacol.* 9(4) S198 (1986). Significant homology was found between the isolates examined and Peptide T when comparison was made with the core pentapeptide, (Ruff et al. *FEBS Lett.* 211 17–22 (1987); Brenneman et al, *Nature*, 335 639–642 (1988); Brenneman et al, *Drug Dev. Res.* 15 361–369 (1988); Kòmisaruk et al, *annals of the NY Acid. Sci.* 527 650–654 (1988); Buzy et al, *The Lancet* 22 July, 226–227 (1989)). This comparison has now been extended to over twenty isolates.

The inhibition of gp120 and HIV binding to CD4, as well as the demonstration of reduced infectivity of HIV in the presence of Peptide T and its analogues, provides one possible mechanism of action to explain the clinical effects of Peptide T. In this regard Peptide T in sufficient concentration may prevent new cellular infection with HIV. Initial research in this area was focused on the CNS for two reasons: a high concentration of CD4 molecules was found on neurons and one of the major effects of HIV infection is the development of neurocognitive dysfunction. These fats are particularly important given that Peptide T is transported from the blood to the brain by an active, saturable transport system, while its exit is by diffusion only, (Barrera et al, *Brain Res. Bull.* 19 629–633 (1987)).

Although it is well accepted that HIV can infect not only lymphocytes but also neurons, it is difficult to ascribe the neurologic dysfunction seen in HIV patients to active CNS HIV infection, since only a small number of neurons are actively infected. If has been suggested that the neurological deficits seen in HIV infection may occur not only as a result of infection but also as a result of a viral "toxin", such as gp120. Brenneman et al, *Nature* 335 639–642 (1988)) found that purified gp120 from two isolates as well as recombinant gp120 produced significant neuronal cell death in cultures of mouse foetal hippocampal neurons. Neurotoxicity could be reduced by pretreatment with antibody to CD4 and was completely eliminated by VIP. Since mouse neurons cannot be infected with HIV, it is evident that neurotoxicity is gp120-induced and is not a result of viral entry or replication.

VIP (66, 66, 68, 69: TDNYT) and the core peptide (61–65; TTNYT) share the nomologous sequence that binds CD4, and that is also found in isolates of the much larger gp120. Peptide T, when used in the same mouse hippocampal neuronal culture system, completely, antagonised the gp120-induced neurotoxicity, Brenneman et al, *Drug Dev. Res.* 15 361–369 (1988)). In addition, CSF from a patient with AIDS dementia produced substantial neurotoxicity in this system (44–49% killing at 1:100,000 dilution). This effect was inhibited by Peptide T. Buzy et al, *The Lancet*, July 22, pp 226–227, (1989)). Normally gp120 is produced in vast excess of amounts required for viral replication; this excess gp120 may exert a neurotoxic effect far out of proportion to the number of microglial cells or neurons actively infected with HIV.

Peptide T may act as an agonist in addition to or even in the absence of its neuroprotective effects against viral infection and neurotoxicity. Direct agonist activity has been demonstrated in two ways. Ruff et al, (*FEBS Lett.* 211 17–22 (1987)) showed that Peptide T and two analogues were potent agonists of human monocyte chemotaxis. Their rank order potency as chemotactic agents corresponded to their relative ability to inhibit both gp120 binding and HIV T cell infectivity.

As a further demonstration of the agonist activity of Peptide T, both Peptide T and VIP exert their cellular effects via the regulation of protein kinase C: Zorn et al, *The Endoc. Society. Abstract* (1989)). Agonist activity of Peptide T is thus implied by the production of a transmembrane signal that can influence the regulation of protein kinase C. It has also been demonstrated in six individual experiments, as part of the present invention, that Peptide T can down-regulate the enzyme pub $56^{lck}$, a tyrosine kinase linked to the cytoplasmic portion of membrane-bound CD4, thus implying that the binding of Peptide T to the CN4 molecule can produce a transmembrane signal.

Further evidence of Peptide T's potential VIP-like agonist activity is provided by results from experimental testing of the hypothesis of Komisaruk et al, *Annals of the NY Acad. Sci.* 527 650–654 (1988)) that VIP released from pelvic nerve terminals into the spinal cord can produce analgesia. Knowing that naloxone-independent analgesia produced by administration of VIP to the periaqueductal grey matter in rats had been shown, the investigators administered VIP directly to rat spinal cord and measured the pain threshold to distal noxious stimuli to test the hypothesis. Spinal administration of VIP produced analgesia as measured by the tail-flick latency response and the tail-shock induced vocalisation test by action on both opiate and non-opiate modulated pain pathways. Komisaruk et al, *Annals of the NY Acid. Sci.* 527 650–654 (1988)).

The existence of clinical benefits from the administration of Peptide T to humans has been suggested in all studies to date: in HIV disease, by the Pilot Swedish Study, the USA Phase I and Fenway/CRI studies, and the Toronto Western Hospital Compassionate Use Program involving 51 patients; in psoriasis and other medical conditions, in case reports from Sweden (Marcusson, Lazega et al, 1989–9, and Marcussion and Wetterberg, 189–10) and in 8 patients with psoriasis or other medical conditions in Toronto.

Neurocognitive improvement found in HIV positive patients and improvement in constitutional symptoms in both HIV positive and HIV negative patients may well depend primarily on Peptide T's VIP-Like neurotropic and agonist effects, as well as the anti-inflammatory and anti-TNF effects discussed below.

Not wishing to be bound by any particular theory, with respect to the use of these peptides with treatment of MS and HAM, and in view of the above guidelines and discussions in relation to the use of various peptides of General Formula 2 and their analogues in the treatment of HIV, it is hypothesised that there are numerous similarities of disease expression and potential similarities of disease etiology. Peptide T appears to act as an agonist and as a blocker of CD4- mediated immune function rather than as an antiviral drug. In investigations associated with the present invention, patients with non-HIV disease such as multiple sclerosis, HTLV-1 associated myelopathy, and psoriasis have all been treated with Peptide T.

Now that the effectiveness of the peptides of General Formula 1, and particularly those of General Formula 2, is shown, the following is suggested as a hypothesis as to why the compounds do work:

1) Both HAM and MS are chronic CNS inflammatory and demyelinating diseases as is HIV disease.

2) Both diseases have possible viral aetiologies; it is now generally accepted that HAM is caused by the retrovirus, HTLV-1, a virus in the same family as HIV; MS has also been suggested as a manifestation of HTLV-1 infection and the chronic fatigue syndrome has recently been linked to a number of possible viral infections both of DNA (eg HHV-6) and retroviral aetiologies.

3) The two diseases share a number of common symptoms, for example, fatigue, lack of balance and signs of autoimmune phenomena; it is worth while noting that HTLV-1 disease exhibits numerous signs of autoimmunity such that it may be expected that some retroviral diseases have a concomitant expression in autoimmune phenomena. One common theme among these diseases may be peripheral neuropathy which is based on the process of demyelination.

4) The basis appears to be the common denominator of both demyelination whether it be in the central or peripheral nervous system and the common autoimmune manifestations in HAM, MS and HIV disease.

5) Demyelination is associated with inflammation of any aetiology and appears to be mediated at least in part by TNF.

Not wishing to be bound by any particular theory with respect to the use of peptides with the treatment of symptoms and diseases associated with chronic immune activation, and in view of the above guidelines and discussions in relation to the use of various peptides of General Formula 2 and their analogues in the treatment of HIV, it is hypothesised that there is an immunomodulatory effect of the Peptide T binding to CD4. Such effect is demonstrated in the following examples where Peptide T has been found to inhibit mitogen induced proliferation of peripheral blood mononuclear cells (PBMC) at picomolar and lower concentrations. We have found that Peptide T allowed PBMC to proliferate in response to mitogen, but at a reduced level compared to the growth of PBMC in its absence. Preincubation of PBMC with Peptide T for less than 30 minutes had no effect on mitogen stimulation. However, exposure of PBMC to Peptide T for 2 hours followed by washing of the cells before exposure to the mitogen resulted in inhibition of proliferation similar to that seen when cells are incubated in the presence of both Peptide T and mitogen. It was also found that Peptide T did not significantly affect the growth of PBMC cultured in the absence of mitogen. It is therefore thought that Peptide T is able to suppress the normal proliferative response of PBMC to non-CD4 associated proliferation signals.

Now that the effectiveness of the peptides of General Formula 1, and particularly those of General Formula 2, in treating symptoms and diseases associated with chronic immune activations or chronic inflammation has been discovered, the following is suggested as hypothesis of the mechanism of action of Peptide T and, therefore, why the compounds useful in the invention are effective.

Peptide T binds to CD4. It has been established in the following tests that Peptide T inhibits mitogen and MLR induced lymphocyte proliferation. It is therefore thought that Peptide T may serve as an immunomodulatory drug which would down-regulate the enhanced immune response occurring in the chronic presence of antigen or for other reasons mentioned and hence reduce chronic inflammation.

Underlying all these utilities runs the common theme of inflammation.

In accordance with various embodiments of this invention and in view of the above guidelines gained from the use of peptides of General Formula 1, and particularly those of General Formula 2, in the treatment of HIV, similar doses of Peptide T and its analogues can be administered to humans or other animals for purposes of treating inflammation.

The invention will now be illustrated by the following non-limiting examples. The examples refer to the accompanying drawings, in which:

FIG. 1 is referred to in Example 6 and shows the effect of Peptide T on TNF-induced tissue factor expression on human umbilical vein endothelial cells.

FIGS. 2a, 2b and 2c relate to Example 17 and show that Peptide T was able to inhibit lymphoproliferation in response to mitogens. $10^5$ PBMC were cultured in the presence of PWM (2a), Con A (2b) or PHA (2c) with dilutions of Peptide T as follows: A: no Peptide T; B: $10^{-5}$ M; C: $10^{-7}$ M, D: $10^{-9}$M; E: $10^{-11}$M; F: $10^{-13}$M; G: $10^{-15}$M; H: $10^{-17}$M. Cultures were incubated for 5 days, pulsed with $^3$H-thymidine and the amount of incorporated radioactivity converted into proliferation index as described in Example 17. Asterisk (*) indicates the difference in proliferation; ±is statistically insignificant (p>0.05).

FIG. 3 relates to Example 17 and shows that Con A-induced lymphocyte proliferation in the presence of Peptide T parallels, cut at a reduced rate, growth in the absence of Con A. $10^5$ PBMC were cultured in the presence of Con A for 8 days. Cultures ere pulsed and harvested daily and the degree of lymphoproliferation expressed as counts per minute (CPM) of incorporated $^3$H-thymidine. Peptide T (PT, $10^{-9}$M), was added concurrently with Con A.

FIG. 4 relates to Example 18. In the presence of non-mitogen stimuli such as recall antigens (measles, mumps, rubella vaccine: NMR), superantigens such as Staphylococcal enterotoxins SEB and TSST-1, and antibodies to CD3 (anti-CD3) pBMC will proliferate as indicated by a proliferation index greater than 1 (−Peptide T). The presence of Peptide T (+Peptide T) added on the first day of this six day culture had no effect on the growth of PBMC in response to these stimuli.

FIG. 5 also relates to Example 18. When PBMC from one person (A) are cultured in the presence of PBMC from another person (B) they will proliferate [(A+B(P−PT)] as a result of recognising foreign antigens (alloantigens) on the cell surface. In the presence of Peptide T [A+B(+PT)] alloresponsive cells are still able to proliferate.

FIG. 6 also relates to Example 18. Molt-4 is a spontaneously growing human malignant T cell line. In the presence of PBMC growth is inhibited due to killing of Molt-4 by PBMC (PBMC/Molt-4-PT). In the presence of Peptide T added on the first day of a four day culture, PBMC mediated killing of Molt-4 remained unchanged (PBMC/Molt-4+PT).

FIG. 7 relates to Example 19, in which is given the sequence of steps involved in this cytotoxicity assay. Activated macrophages are able to kill K562 target cells in the absence of Peptide T (noPT). If Peptide T is added to macrophage cultures concurrently with the activators (PTstep1) it is unable to affect cytotoxicity. If Peptide T is added to activated macrophage cultures concurrently with the target cells (PTstep2) cytotoxicity is inhibited. Altering the timing of addition of Peptide T does not alter the Peptide T-mediated inhibition of macrophage-mediated cytotoxicity.

FIG. 8, which also relates to Example 19, shows that the supernatant of macrophage cultures stimulated with LPS contain cytolytic substances capable of killing target K562 cells. Target cells are labelled with intracellular radioactivity that is released upon cell death. More radiolabel release (measured as counters per minute, cpm) indicates more killing. In the absence of Peptide T (A) more killing occurred than in its presence (B-F). As the concentration of Peptide T was dropped below $1 \times 10^{-15}$M cytolytic activity the degree of cytotoxicity returned to control (A) levels. The Peptide T concentrations were as follows:

A: no Peptide T
B: Peptide T, $10^{-5}$M
C: Peptide T, $10^{-7}$M
D: Peptide T, $10^{-9}$M
E: Peptide T, $10^{-11}$M
F: Peptide T, $10^{-13}$M
G. Peptide T, $10^{-15}$M FIG. 9 is referred to in Example 20 and shows that peptide T has a similar effect to anti-TNF in inhibiting the effects of TNF.

Figure 1:
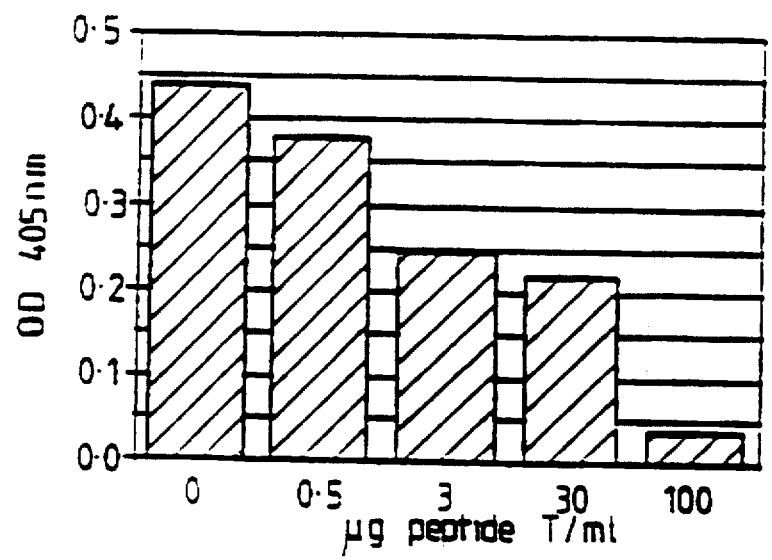

Examples 1 to 4 demonstrate the significant effects that the peptides useful in the invention have clinically on MS and HAM. The peptide used in each of Examples 1 to 4 is a variant Peptide T of General Formula 2 having the sequence D-Ala-Ser-Thr-Thr-Thr-Asn-Tyr-Thr-Amide.

EXAMPLE 1

HTLV-1 MYELOPATHY

A 45 year old female was diagnosed as HTLV-1 seropositive after experiencing dysaesthesia of the feet, pain in the feet and legs, weakness of the legs and urinary frequency. Her neurological examination confirmed increased deep tendon reflexes, spasticity of the lower limbs and pyramidal weakness of the legs. The diagnosis was confirmed by somatosensory and auditory evoked potentials and HTLV-1 seropositivity. Therapy, consisting of 8.5 mg of Peptide T, was self-administered subcutaneously each morning. After two months of taking Peptide T, she stated that she was substantially improved and now able to lift both feet instead of dragging them along the floor. In addition, she was to work without a cane, could stand without the support of a walker or cane, could climb stairs for the first time in two years and reported decreased burning pain in the feet to the knees and reported decreased urinary frequency and nocturia. Her most functionally debilitating symptom had been the painful peripheral neuropathy which had severely limited her mobility and had limited her social contacts and disturbed her sleep; she described the pain as severe to intolerable. The pain, previously refractory to known therapy, became manageable, tolerable and of minor significance to daily function.

After a subsequent to months of Peptide T therapy, which was her only new medication, she reported continual decrease in symptoms and continuing improved mobility. Her neurological examination remained unchanged other than her improved functional capacity, eg walking.

Although previously confined to her apartment, her improved post-treatment mobility enabled her to travel to her Caribbean home. During this trip she used her entire supply of drug and within five days noted progressive fatigue and became bed-bound with fatigue, weakness and pain. Within two weeks of stopping Peptide T, her symptoms essentially resolved within one month. On two subsequent occasions she terminated treatment, with similar recurrance of symptoms and similar resolution upon reinstitution of Peptide T therapy.

EXAMPLE 2

MULTIPLE SCLEROSIS

A 40 year old female was diagnosed as having MS after presenting with weakness, loss of balance, double vision, and paraesthesia in her right arm at age 23. She was treated with prednisone and later with physiotherapy, with little effect. Upon presentation, she remained unable to walk without a cane or a walker, showed depression, horizontal nystagmus, and weakness of hip flexors bilaterally, weakness of knee flexors and of dorsilflexors of the feet. Tone was increased in both lower limbs and she had bilateral ankle clonus. Deep tendon reflexes were 2+ in the arms, 3+ in both knees and ankles and the plantar responses were extensor. She was treated with LIORESEAL™ (baclofen) with some improvement; however, she experienced progressive worsening until she became wheelchair dependent and complained of weakness, spasticity, clonus, urinary incontinence and recurrent urinary tract infections. When she was evaluated her MRI brain scan showed findings consistent with multiple sclerosis.

She was started on Peptide T, 8.5 mg subcutaneously daily. She reported that many of her symptoms including spasticity, fine motor co-ordination, nocturia and urinary frequency, concentration, memory and emotional lability had greatly improved. She was assessed after five weeks of treatment and both reported and demonstrated functional improvement. After six months, she demonstrated sustained improvement in these symptoms. Her frequency of nocturia was reduced, fine motor control improved, stuttering decreased, her legs were less spastic and she could stand with minimal support. She showed marked symptomatic improvement in intellectual and motor functioning within a few weeks after starting treatment with Peptide T, such improvement being sustained over a 6 month period. Worsening of symptoms occurred when the patient stopped Peptide T for 3 weeks, but improved when she restarted the drug. The patient has remained stable rather than following her normal progressive downhill course for the months she has remained on Peptide T.

EXAMPLE 3

Multiple Sclerosis

A 28 year old female was diagnosed with optic neuritis secondary to multiple sclerosis after presenting with numbness, impaired motor function, and blurred vision (20/300 bilaterally). Her somatic neurological examination was within normal limits. Minor episodes of numbness and impaired speech, balance and co-ordination had occurred over 6 months, as well as headache and loss of vision.

Peptide T therapy was started. Six days later a reassessment showed remarkably improved visual acuity (21/30) bilaterally). The patient noted functional improvement over the next week. A prior episode of optic neuritis took six months to recover (compatible with the natural history of MS) compared to this episode which recovered much more quickly than would be expected for an episode of MS-induced optic neuritis.

EXAMPLE 4

MULTIPLE SCLEROSIS

A 34 year old woman with her first episode of multiple sclerosis as manifest by optic neuritis and complete blindness in the right eye for 2 weeks, numbness in her right leg and then both legs. Her symptoms worsened and she was given prednisone and experienced some improvement. She had worsening of her ataxias with blurred vision and oscillopsia and was given prednisone 80 mg per day. An MRI scan showed multiple high intensity signals periventricularly as well as in the brain stem consistent with the diagnosis of MS. The ataxia and some visual problems seemed to improve on steroids. Another MRI scan about 16 months later showed extensive periventricular white matter disease with involvement of the corpus collosum. Findings were typical of demyelination consistent with MS. At that time the patient showed resting oscillatory lateral beating nystagmus and lateral nystagmus with bilateral gaze, an ataxic gait, a slight impairment on her heel shin test but good finger nose testing. The tone was increased in her lower limbs and she had non-substained ankle clonus bilaterally. Her knee jerk was increased on the right compared to the left. Plantar responses were both upgoing. She had decreased position, vibration, light touch and cold sensation in the feet compared to the hands.

About 2 months later the patient was started on Peptide T 8.5 mg subcutaneously daily. Within 1 to 2 weeks the reported subjective improvement. She experienced improved feelings in her fingers, fine movements of her hands and improved cognitive function. When she stopped Peptide T therapy she noticed an increased fatigue and ataxia. She obtained minimal symptomatic improvement from prednisone 150 mg daily. After restarting Peptide T, she noted a remarkable improvement of her fatigue, ataxia and fine motor function.

EXAMPLE 5

MULTIPLE SCLEROSIS

A 56 year old female with a history of dizziness, ataxia, episodes of vertigo, impairment of motor function and generalized weakness of the legs was treated with dilantin and admitted to hospital. Subsequent examination showed vertical nystagmus, some saccadic smooth pursuit and an impaired tandem gait. She was reassessed about 2 years later for episodes of dizziness, and complaints of leg spasms. Her physical examination showed decreased visual fields with a partial left lateral hemianopsia in the lateral field and a right constricted field. She showed impaired tandem gait, decreased right hip flexion and strength and decreased deep tendon reflexes in the right brachioradialis compared to the left and in the right knee compared to the left. Plantar response was down going and she had upwards gaze vertical nystagmus as previously noted.

The patient began peptide T 8.5 mg subcutaneously daily and within 10 days reported increased energy and intellectual function, and improved vision. When Peptide T therapy was stopped, she regressed symptomatically to her pre-drug status. Her physical examination at that time showed no change from her examination before Peptide T therapy was begun.

Examples 5 to 7 show experimentally certain significant effects exhibited by peptides useful in the invention.

EXAMPLE 6

LPS-INDUCED INFLAMMATION

Normal balb/c mice (female, 12 weeks) were administered LPS (250 µg, $E.\ coli$ K-235, Sigma cat. no. L-2018) at time zero. One group of mice (50 animals) were then treated at 30 minutes intervals by i/p. injections of bovine serum albumin (BSA) (Sigma cat. no. 6793) dissolved in pyrogen-free, sterile, isotonic water (2.5 mg BSA per animal per injection, each injection containing 100 µl).

The second group of mice (50 animals) were treated at 30 minutes intervals by i.p. injections of Peptide T (Carlbiotech A/S batch 109401) dissolved in pyrogen-free, sterile, isotonic water (2.5 mg Peptide T per animal per injection, each injection 100 µl).

Glucose levels were determined on blood samples after 3 hours. Subjecting parameters such as secretion from the eye, diarrhoea and general well being are indicated on a scale of (−) to (+++).

As can be seen from Table I, the difference in glucose levels between Peptide T-treated animals and BSA- (placebo) treated animals is highly significant. The subjective parameters also strongly indicate a general higher index of well being for animals treated with Peptide T.

TABLE I

|  | Diarrhoea | | Blood Glucose | | Secretion from eyes | | General well being | |
|---|---|---|---|---|---|---|---|---|
|  | '0 | '3 hrs | '0 | '3 hrs | '0 | '3 hrs | '0 | '3 hrs |
| Control (BSA) | − | +++ | 4.4 = 0.7 | 2.0 = 0.2 | − | +++ | − | +++ |
| Peptide T treated | − | + | 4.3 = 0.6 | 2.4 = 0.5 | − | + | − | + |

$^1$test = 98 p < 0.001 for peptide T treated group vs. control (BSA-treated group).

EXAMPLE 7

PEPTIDE T ANTAGONISES TNF

Stimulation of endothelial cells with TNF results in the induction of procoagulant activity through the expression of tissue factor activity and a concomitant reduction of the anticoagulant potential of the cells through reduced expression of thrombomodulin (Bevilacque et al, Nawroth and Stern, *J. Exp. Med.* 163 740 (1986)). Septic shock is frequently accompanied by disseminated intravascular coagulation (DIC. Semeraro *Acta Clinica Belgica* 31 377 (1976) and there is considerable evidence that tissue factor is an essential requirement for DIC to be induced by endotoxin (LPS). A monoclonal antibody against tissue factor has been shown to inhibit DIC induced by the administration of endotoxin (Warr et al, *Blood,* 75 1481 (1990).

Human umbilical vein endothelial cells were cultured in M199 medium supplemented with 10% foetal calf serum, endothelial cell growth factor, penicillin, streptomycin and L-glutamine in 96-well dishes using a modification of the procedure of Bevilaqua et al., Proc. Natl. Acad. Sci. USA 83 4533 (1986)). TNF treatment of cultures (100 units.ml) was for 4 h at 37° C. in the presence of growth medium, after which the cells were washed and fixed. Cultures were also treated with Peptide T+TNF or Peptide T alone. In these cultures Peptide T was at a concentration which ranged from 0.5 to 100 µg/ml. Tissue factor expression by the endothelial cells treated with TNF with or without peptide T was determined in an ELISA using a monoclonal antibody which neutralises the activity of human tissue factor (Carlbiochem A/S). Bound anti-tissue factor antibody was detected using peroxidase-conjugated rabbit anti-mouse Ig and the substrate ABST. Colour intensity was determined by the optical density of each well at 405 nm.

The data obtained from triplicate cultures show that peptide T inhibited the expression of tissue factor on endothelial cells stimulated by 100 units/ml human recombinant TNF and are illustrated in FIG. 1.

EXAMPLE 8

PEPTIDE T INSTIGATES LPS-INDUCED MORTALITY

Mice bearing Meth A ascites tumours were given 100 µg LPS subcutaneously with either bovine serum albumin (BSA) or peptide T analogue (504 or 505, 1 mg). The number of animals showing signs of LPS toxicity (diarrhoea, exudate from the eyes and general level of activity) in each group was recorded at 19, 24 and 41 hours after injection. At the completion of the experiment the number of surviving animals was recorded (see Table II below) and the survivors bled for later determination of TNF, IL-1, IL-6 and RNI levels.

The sequence of the most effective analogue (505 is:

H-D-Ser-Ser-D-Thr-Thr-D-Thr-Thr-Tyr-D-Thr-NH$_2$(SEQ ID NO:11)

and the sequence of the 504 is:

H-D-Ala-Ser-D-Thr-Thr-D-Thr-Asn-Tyr-D-Thr-NH$_2$(SEQ ID NO:10)

TABLE II

EFFECTS OF PEPTIDE T ANALOGUES ON SURVIVAL OF LPS-TREATED TUMOUR BEARING MICE

| Treatment | % mice surviving 41 hours | % mice with diarrhoea at 19 hrs | % mice with exudate at 19 hrs |
|---|---|---|---|
| LPS + BSA | 60 | 100 | 100 |
| LPS + 505 | 100 | 40 | 20 |
| LPS + 504 | 100 | 40 | 60 |

Examples 9 to 15 illustrate the effectiveness of peptides useful in the invention in relation to various diseases and/or symptoms associated with chronic inflammation.

EXAMPLE 9

INHIBITION OF MITOGEN INDUCED PROLIFERATION OF PBMC

PBMC ($10^5$) were cultured in 200 µl RPMI containing 10% heat inactivated foetal bovine serum, 2 mM L-glutamine and gentamycin 100 µg/ml with mitogen and Peptide T added on the first day of culture. Growth was assessed in triplicate by $^3$H thymidine uptake following a 6 day incubation and expressed as a proliferation index (cpm in presence of mitogen±Peptide T−cpm in absence of stimulation). A proliferation index >1.00 implies growth beyond that in media alone. At physiologically obtainable concentrations, Peptide T inhibits proliferation of normal (HIV seronegative) peripheral blood mononuclear cells (PBMC) without causing significant cytotoxicity as shown in Table III. This effect is long term in that Peptide T given on the first day of a six day culture will inhibit mitogen induced proliferation.

TABLE III

| | Proliferation Index ± SD[1] | | | |
|---|---|---|---|---|
| Peptide T[2] | Media[3] | PWM[4] | ConA[4] | PHZ[4] |
| 0 | 1.00 | 7.47 ± 0.50 | 4.55 ± 0.66 | 317.0 ± 41.0 |
| $10^{-5}$ | 1.14 ± 0.15 | ND[5] | 2.72 ± 1.20 | 149.0 ± 38.4 |
| $10^{-7}$ | 0.73 ± 0.16 | 4.47 ± 0.36 | 3.19 ± 0.06 | 123.6 ± 18.1 |
| $10^{-9}$ | 2.17 ± 1.10 | 4.69 ± 0.42 | 1.98 ± 0.04 | 78.6 ± 23.1 |
| $10^{-12}$ | 1.52 ± 0.15 | 4.15 ± 0.23 | 1.69 ± 0.48 | 103.8 ± 22.8 |

[1]SD—standard deviation
[2]Concentration of peptide T in mol/l
[3]Growth in absence of mitogens
[4]Pokeweed mitogen (PWM), Concanavalin A (Con A) and phytohemagglutinin (PHA) were used at 25 µg/ml
[5]ND—not done 1. SE—standard deviation
2. Concentration of peptide T in mol/l
3. Growth in absence of mitogens
4. Pokeweed mitogen (PWM), Concanavalin A (Con A) and phytohemagglutinin (PHA) were used at 25 µg/ml
5. ND—not done

EXAMPLE 10

INHIBITION OF MLR

A two way MLR was performed using $10^5$ allogeneic PBMC (cpm of A=142±86, B=148±84) cocultured in 200 µl of media as described in Table III.

Peptide T given on the first day of an MLR will inhibit allogeneic induced proliferation of PBMC (Table IV).

TABLE IV

| | Inhibition of MLR |
|---|---|
| Peptide T[1] | cpm ± SD[2] |
| 0 | 1365 ± 335 |
| $10^{-5}$ | 649 ± 263 |
| $10^{-7}$ | 534 ± 108 |
| $10^{-9}$ | 764 ± 77 |
| $10^{-11}$ | 681 ± 222 |
| $10^{-13}$ | 235 ± 4 |
| $10^{-15}$ | 371 ± 117 |
| $10^{-17}$ | 672 ± 261 |

[1]Concentration of peptide T in mol/l
[2]Counts per minute ± standard deviation

EXAMPLE 11

EFFECT OF PEPTIDE T ON ACTIVITY OF p56$^{lck}$ IN PBL blasts

PBL (peripheral blood leukocyte) blasts were prepared by incubating PBMC at 37° C. with PHA (10 µg/ml) in RPMI+

10% FBS for 48 hours followed by addition of interleukin-2 and incubation for a subsequent 96 hours. Cells were washed free of IL-2 and incubated for 24 hours then washed free of FBS and incubated for 24 hours. PBL blasts remained either stimulated or were treated with OKT4A (anti-CD4) at 10 µg/ml for 1 hour followed by rat anti-mouse Ig at 5 µg/ml for 5 minutes to enhance lck activity. PBL blasts were pretreated with Peptide T ($10^{-9}$ M) for 2 hours, then washed extensively before anti-CD4 stimulation. Following immunoprecipitation with anti-lck-Protein A conjugates and incubation (37° C. 10 minutes) with $^{32}$P-ATP. $p56^{lck}$ autophosphorylation was determined by autoradiography and used as a measure of $p56^{lck}$ activity.

Peptide T will inhibit the PHA-induced activation and anti-CD4 dependent enhancement of $p56^{lck}$ activity as we have determined (Table V) by an lck specific tyrosine kinase assay. $p56^{lock}$ is a CD4 associated tyrosine kinase involved in T cell activation and transmembrane signalling (Janeway C. A. Ann. Rev. Immunol. 10 645–474 (1992)). In lieu of a T cell receptor associated signal, cross-linking of CD4 by monoclonal anti-CD4 inhibits T cell activation (Burgess et al. Eur. J. Immunol. 21 1663–1668 (1991)), possibly by activating $p56^{lck}$ including autophosphorylation of the inhibitory Tyr 505 (Abraham et al. nature 350 62–66 (1991); Abraham et al. Cancer Invest. 9 455–463 (1991)). Peptide T is able to inhibit $p56^{lck}$ activation (Table V) thus achieving the same result as anti-CD4 (inhibition of T cell activation) although by a different mechanism.

TABLE V

EFFECT OF PEPTIDE T ON ACTIVITY OF $p56^{LCK}$ IN PB< BLASTS

| Unstimulated | | Anti-CD4 | |
|---|---|---|---|
| –P.T.[1] | +P.T. | –P.T. | +P.T. |
| +++[2] | + | ++++ | ++ |

[1] P.T. means Peptide T
[2] +++ highly active
+ slightly active

It is known that anti-CD4 antibodies will inhibit mitogen-induced as well as and antigen-induced in vitro proliferation of PBMC, lymphokine release, T helper function and MLR (Bank et al. J. Exp. Med. 162 1294–1303 (1985)). There are two possible mechanisms of anti-CD4 inhibition of T cell function.

1) Anti-CD4 antibodies cause steric hinderance of the CD4/MHC II interaction that occurs during T cell activation. Peptide T would probably not share this effect since it is derived from a sequence of gp120 known to bind to CD4 and this binding site of gp120 on the CD4 molecule is distant from the MHC II binding site (Fleury et al (1991)).

2) Cross-linking of CD4 by multivalent anti-CD4 antibodies, in lieu of TcR/CD3 stimulation sends a negative signal to the T cell (Bank et al, J. Exp. Med. 162 1294–1303 (1985)). Peptide T is monovalent, hence cannot cross-link CD4 receptors; therefore, its mechanism of inhibition of T cell activation must be distinct from that of anti-CD4. Treatment of inflammatory conditions with mouse anti-CD4 has resulted in a number of undesirable side effects including urticaria, chills, fever and tremors that occasionally require medical intervention. In addition, following administration of anti-CD4 there has been reported a reduction in CD4 cell numbers, a reduction in proliferation to mitogens and antigens and a reduction in delayed hypersensitivity reactions, a measure of cell mediated immune function (Horneff et al. Cytokine 3 266–267 (1991); Horneff et al, Arth. Rheum. 34 129–140 (1991); Wofsey et al. Semin. Immuno. 2 419–425 (1990)). Administration of anti-CD4 concurrently with antigen can inhibit both primary and secondary immune responses (Waldor N. K. Immunol. Ser. 45 573–586 (1990)). In addition, the use of xenogeneic (non-human) proteins as therapeutic agents is limited due to the potential formation of antibodies directed against the foreign protein which can mediate shock and type III hypersensitivity reactions upon repeated administration.

EXAMPLE 12

EFFECT OF PEPTIDE T ON ANTIGEN INDUCED PBMC PROLIFERATION

PBMC were incubated as described in relation to Table III in Example 9 in the presence of live, attenuated measles, mumps and rubella vaccine (Merck Sharp and Dohme, Canada) at a final dilution of 1:20. Peptide T was added either on day 1 of incubation or on a daily basis. Results are expressed as a proliferation index±standard deviation.

TABLE VI

EFFECT OF PEPTIDE T ON ANTIGEN INDUCED PMBC PROLIFERATION

| Conc. Peptide T | Proliferation Index ± S.D. | |
|---|---|---|
| (Mol/L) | Day 1 | Daily |
| 0 | 3.26 ± 0.55 | |
| $10^{-7}$ | 4.02 ± 0.78 | 1.83 ± 0.36 |
| $10^{-9}$ | 1.91 ± 0.46 | 0.98 ± 0.16 |
| $10^{-11}$ | 5.35 ± 1.46 | 1.56 ± 0.14 |
| $10^{-13}$ | 5.46 ± 1.37 | 1.38 ± 0.51 |
| $10^{-15}$ | 5.56 ± 0.60 | 1.56 ± 0.61 |
| $10^{-17}$ | 3.99 ± 0.18 | 1.60 ± 0.60 |
| $10^{-19}$ | 6.15 ± 2.59 | 2.27 ± 1.09 |

Although Peptide T can inhibit antigen-induced proliferation of PBMC when administered in vitro on a daily basis, we do not believed this will have any significant effect on the normal immune response when administered in vivo (as demonstrated by Goodwin et al V. International Conf. Aids. Montreal, July 1989 Abstract #WBP286). There are two possible explanations for this that are not mutually exclusive.

1. Macrophages may be more sensitive to Peptide T than are T cells, since T cells receive many more potential activating signals than the CD4/MHC II interaction. Thus macrophages may be down regulated by Peptide T administration on the first day of in vitro culture inhibiting their ability to present mitogens and antigens to T cells. B cells can act as APC in pace of macrophages when presenting antigen, but not when presenting mitogens which are antigen non-specific (explaining the results of Table III). Resting B cells are resistant to Peptide T as they are CD4 negative. In the presence of a single dose of Peptide T, they could present antigen to T cells allowing proliferation of PBMC in response to antigen. When Peptide T is given on a daily basis in cultured T cells, which may be less sensitive to the effects of Peptide T, then macrophages may be inhibited. This would explain the results shown in Table 4. Daily administration of Peptide T in vivo may not function as it does on a daily basis in vitro, since the half life of Peptide T in vivo is shorter than in vitro. In vitro serum supplements are heat inactivated to destroy propteolytic enzymes which actively degrade Peptide T in vivo. Thus daily administration of Peptide T in vivo would result in the inhibition of macrophage activity, but not T cell activity and would allow the continued expression of antigen driven immune responses. This would explain the efficiency of Peptide T in chronic inflammatory conditions such as rheumatoid arthritis (see blow; where the characteristic inflammatory cell is the macrophage. Acute inflammation is characterised by neutrophil (CD4 negative) infiltrates and would not be affected by Peptide T administration. The requirement for antigen presentation (phagocytosis, degradation and presentation) in an antigen driven immune response results in a daily in T cell signalling. Hence Peptide T present on the first day of in vitro culture will not affect T cell signalling on subsequent days. Mitogen stimulation of PBMC proliferation (Table II) is an immediate event not requiring antigen processing and may be inhibited on a long term basis by concurrent Peptide T administration. Peptide T needs to be present concurrently with an activating signal to manifest its immunodepressive effects. During chronic inflammation or immune activation, all responding cells will be receiving proliferation signals all the time. Daily Peptide T administration in vivo will inhibit chronic immune activation. Since the half life of Peptide T is <1 hour (Ruff et al. *Prog. Neuro-Psychropharmacol & Biol. Psychiat* Vol. 15, pp 791–801 (1991)), those proliferation signals active during the first hour after Peptide T administration will be inhibited. Since all cells responding to chronic activation signals respond all the time, they will be down regulated during this 1 hour period and remain down regulated on a long term basis. Due to the discrete timing of antigen presentation and the fact that not all epitopes of the antigen are presented at the same time (therefore not all T cells capable of responding are activated at the same time), there are 23 hours before the next injection of Peptide T in which to mount antigen specific immune responses. Although some antigen specific immune responses may be inhibited in the 60 minutes post Peptide T administration, the majority which are happening at discrete times, will be allowed to proceed.

In this fashion, Peptide T is able to inhibit chronic immune activation and inflammation while allowing the expression of antigen specific immune responses.

EXAMPLE 13

ARTHRITIS

A 67 year old man was treated with daily Peptide T (8.5 mg s.c.) for severe psoriasis refractory to all known treatment. In addition, be complained of painful arthritis of the knees which although present for over 10 years had progressed to the point of preventing him from participating in his normal daily activities for six months prior to this first visit. Although his psoriasis was only transiently improved by Peptide T, knee pain began to resolve three weeks after starting on the drug. The patient remained pain free for the three months he continued on Peptide T. He was still pain-free at his last follow up two months after discontinuing Peptide T and he had been able to resume daily physical activities. He remained pain free eight months after discontinuing Peptide T. The severity of his arthritis was such that, prior to Peptide T, he had been advised to have knee joint replacement. This dramatic relief from pain is extraordinarily rare in patients with erosive rheumatoid arthritis even when treated aggressively with conventional therapies. His only medication during this time was a non-steroidal anti-inflammatory drug which he had been taking for the previous two years.

EXAMPLE 14

ARTHRITIS

A 47 year old woman was diagnosed as having facet joint arthritis in 1977 with recurrences on a number of occasions the following year. A back education program and exercises resulted in remission until 1992. Following a compressive spinal injury in May 1992, the fact joint arthritis recurred manifest as intense hyperaesthesia of the left hip and though progressing within 8 hours to involve the entire upper leg, characteristic of previous episodes which usually took 3–4 weeks to resolve on bed rest and non-steroidal anti-inflammatory medication. The following day the pain intensified and was characterised as an intense burning sensation accompanied by severe pain in the lumbar region unaffected by Toradol or Naproysn at full dose. The patient was bedridden the following day and sleep disturbance was severe through the following 48 hours. Five days after the episode the patient was given the MOS questionnaire for chronic disease and chronic back pain with an unweighted average score of 40.77 out of 100. Later that day, Peptide T was given (10 mg s.c.) with diminution of the hyperaesthesia and facilitated sleep within 12 hours. Oral medications were discontinued. By the following day, the hyperaesthesia had resolved, sleep was normal and only very mild pain was present in the paraspinal muscles. Peptide T was given for the subsequent 2 days with total relief of pain and improving MOS scores of 71and 87.4 (this score is comparable to a population with no acute or chronic illness). Peptide T was continued for a total of 10 days. On discontinuation, the hyperaesthesia returned and Naprosyn and Toradol were reinstituted with no noticeable effect for 2 days. Peptide T was resumed as the only medication for the next four days with complete relief of pain and hyperaesthesia and reinstitution of normal sleep habits. On discontinuation of Peptide T 5 days later, no recurrence of the symptoms occurred and no oral medication was required.

EXAMPLE 15

CHRONIC FATIGUE SYNDROME

A 45 year old woman with CFS presented with severe fatigue requiring frequency naps, headache, tinnitus, episodic diarrhoea, depression, lightheadedness and a reduction in auditory working memory. She was started on daily Peptide T (8.5 mg s.c.) and noticed improvement within one week. After two months she reported that 50% of her day was normal. Her fatigue had reduced and remaining fatigue was associated only with increased activity possible only after starting Peptide T. Her memory improved and headaches became less frequent. Three months after starting on the drug she was still improving. She could walk for extended periods for the first time in two years and the frequency of her headaches was reduced almost to zero. After five months on the drug, her fatigue had resolved, she experienced no lightheadedness and was gardening, caring for her children and driving distances again.

EXAMPLE 16

CHRONIC FATIGUE SYNDROME

A 32 year old, EBV+ woman presented with a four month history of severe fatigue that prevented her from working more than 1½ hours per day. A putative diagnosis of post-infectious neuromyasthenia was made based on fatigue, decreased concentration, slowness of thought, myalgias and sore throat. Within five days of Peptide T administration (8.5 mg daily s.c.) her fatigue had remarkably decreased and had fully resolved within one month to the point that she was able to resume work fulltime and attend the gym three times per week. She remained on Peptide T for 35 days and she has remained asymptomatic for six months. The Patient Symptom Inventory (a self rating instrument which measures symptom severity on a scale of 0 to 4) was administered before Peptide T was begun and after 30 days of treatment revealed marked improvement in all symptoms:

|  | Day 0 | Day 30 |
| --- | --- | --- |
| Fatigue | 0 | 3 |
| Stamina | 0 | 2 |
| Concentration | 2 | 3 |
| Slowness of thought | 1 | 3 |
| Difficulty word finding | 2 | 4 |

Peptide T appears to act as an anti-inflammatory agent. Peptide T would therefore be a novel non-steroidal anti-inflammatory drug (NSAID). Tradiational NSAIDs, such as aspirin and ibuprofen, have two potential mechanisms of action: inhibition of cyclooxygenase reducing prostaglandin production and inhibition of neutrophil function (Altman R. D. *Arth. Rheum.* 19 (Suppl. 2) 1–5 (1990); Vane et al. *Postgrad. Med J.* 66 (Suppl. 4) S2–S17 (1990)). It had been reported that inhibition of cyclooxygenase will enhance (rather than suppress) mitogen driven PBMC proliferation (Vane et al. *Int. J. Immunopharmacol.* 5 107–114 (1983)) and neutrophils (CD4 negative) would be resistant to Peptide T; therefore, Peptide T may have a unique mechanism of anti-inflammatory action.

The anti-inflammatory azathioprine inhibits lymphocyte proliferation by inhibiting DNA and RNA synthesis. The proliferation of both B and T lymphocytes are inhibited by the action of azathioprine (Briggs J. D. *Immunol. Lett.* 29 89–94 (1991)). Since B cells are CD4 negative and can function as APC in the presence of Peptide T (see above). Peptide T must have a mechanism of action distinct from that of azathioprine.

Cyclosporine is an anti-inflammatory drug that inhibits lymphocyte proliferation by inhibiting IL-2 and IFN γ gene transcription by binding to and inactivating cyclophilin, an isomerase required for signal transduction (Halloran et al., *Clin. Biochem.* 24 3–7 (1991)). While Peptide T may also affect signal transduction (Table 3), id does not have the severe side effects associated with cyclosporine therapy. Cyclosporine induced side effects include renal tubular atrophy, nephrotoxicity, hypertension, hirsutism, gingival hypertrophy, tremors, convulsions and paresthesia (Briggs J. D. *Immunol. Lett.* 29 89–94 (1991). In the experience of the present invention, no significant side effects have been attributable to Peptide T therapy.

EXAMPLE 17

PEPTIDE T INHIBITS MITOGEN-INDUCED LYMPHOPROLIFERATION

Concanavalin A (Con A), pokeweed mitgoen, (PWM) and phytohaemagglutin-P (PHA-P) were obtained from Sigma chemical Co. (St. Louis, Mo. USA). Peptide T was synthesised by Carlbiotech Ltd (Copenhalgen, Denmark) and supplied as the chloride salt at 8.5 mg/ml in 0.9% benzyl alcohol as preservative and was stored at 4° C. Peptide T was diluted to working solutions in culture medium (RPMI). Dilute solutions of Peptide T were prepared fresh from stock Peptide T for each experiment. $^3$H-thymidine (5 Ci/mmol) was obtained from Amersham.

Isolation of PBMC: While blood from healthy, adult volunteers was drawn into heparin and peripheral blood mononuclear cells (PBMC) isolated by density gradient centrifugation on HISTOPAQUE™ (Sigma Chemical Co). PBMC were removed from the interface, washed three times in RPMI containing gentamycin (100 μg/ml) and resuspended to $1 \times 10^6$ PBMC/ml in RPMI containing 10% foetal bovine serum and gentamycin. $10^5$ PBMC were cultured in the presence of 100 μl of mitogen suspension in 96 well plates. The final concentration of mitogen was: PWM 25 μg/ml; PHA 12.5 μg/ml and Con A 6.25 μg/ml. 10 μl of Peptide T working solution (or RPMI as negative control) was added and cell cultures incubated for a total of 5 days in a humid atmosphere, 5% $CO_2$, 37° C. Cultures were then pulsed with $^3$H-thymidine (in RPMI) 18–24 hours prior to harvesting. The amount of incorporated $^3$H-thymidine was determined using a BECKMAN™ LS8000 liquid scintillation counter and proliferation expressed as either counts per minute (cpm) or as a proliferation index (PI).

$$PI = \frac{\text{cpm of }(PBMC + \text{mitogen})}{\text{cpm of}(PBMC + \text{media})}$$

A FI of 2 indicates that cells have grown to twice their resting (unstimulated) number.

All experiments were performed in triplicate. Results reported are characteristic of replicated experiments.

Production of Tumour Necrosis Factor α (TNFα): $5 \times 10^6$ PBMC/ml were incubated in the presence of Con A (6.25 μg/ml) for 48 hours in a humid atmosphere, 5% $CO_2$, 37° C. Peptide T ($10^{-9}$M) was added at t+0 and 24 hours. At the end of incubation, SEPHADEK™ G25 (Pharmacia) was added (10 mg/ml) and incubated for 10 minutes to remove mitogen. PBMC and SEPHADEX were pelleted by centrifugation and the supernatant tested for levels of TNFα using a TNFα radioimmune assay kit from Amersham. Samples were analysed in duplicate.

*Statistical Analyses:* Data were analysed by a two sample ANOVA test using 95% confidence limits such that a value of $p \leq 0.05$ was considered a significant difference.

TABLE VII $1 \times 10^5$ PBMC were cultured in the presence of mitogens with Peptide T ($1 \times 10^{-5}$M) added concurrently with mitogens (Day 1) or on subsequent days as indicated. Cells were cultured for a total of 6 days. Results are expressed as proliferation index ± standard deviation.

|  | PWM | Con A | PHA |
| --- | --- | --- | --- |
| no Peptide T | 4.29 ± 0.25 | 21.0 ± 5.7 | 197 ± 3 |
| Peptide T: |  |  |  |
| Day 1 | 3.13 ± 0.21 | 6.2 ± 0.5 | 148 ± 13 |
| Day 2 | 3.20 ± 0.20 | 6.0 ± 1.1 | 101 ± 7 |
| Day 3 | 2.65 ± 0.17 | 9.9 ± 0.1 | 148 ± 7 |
| Day 4 | 3.22 ± 0.28 | 9.5 ± 1.6 | 131 ± 10 |

Results

Figure 2A:
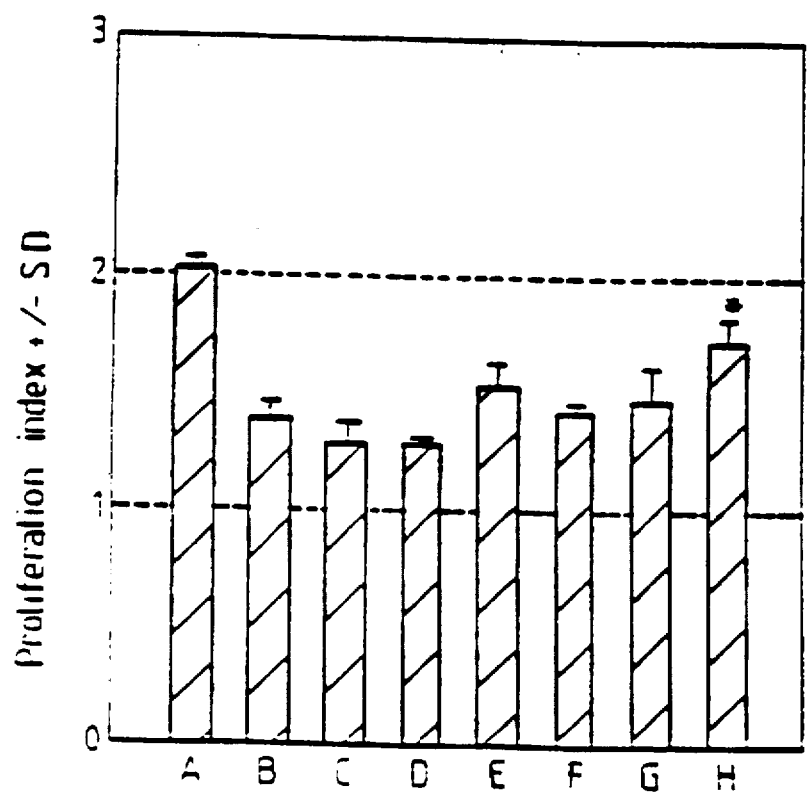
Figure 2B:
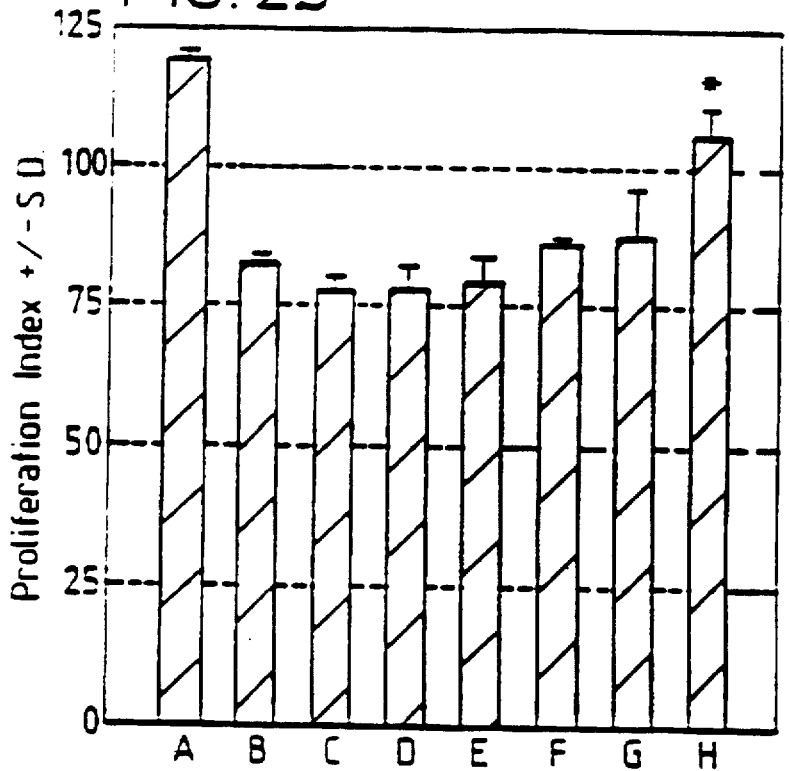
Figure 2C:
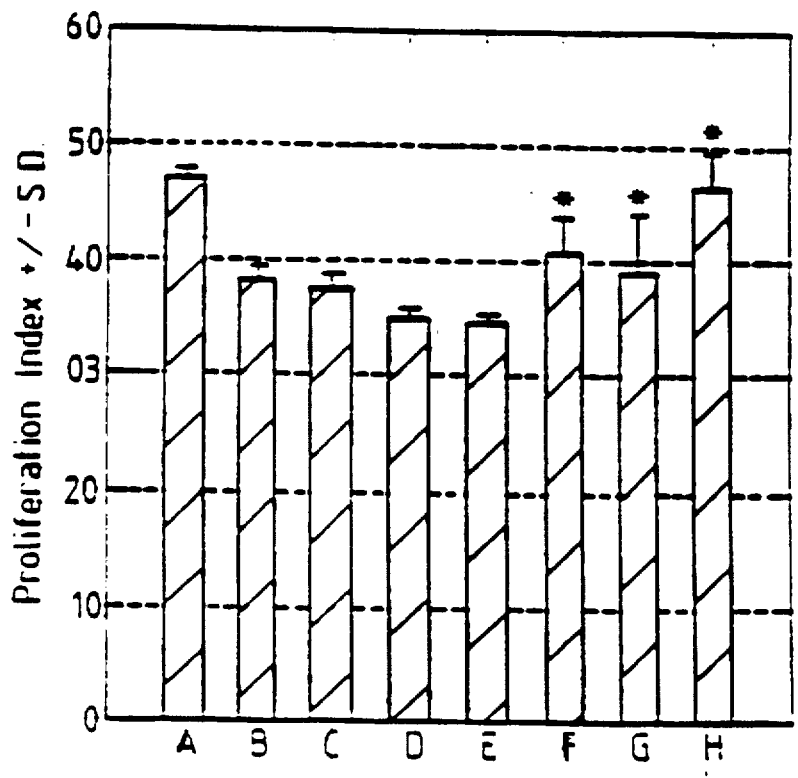

When added on the first day of culture, Peptide T was able to inhibit lymophoproliferation in response to PWM (FIG. 2a). Con A (FIG. 2b) and PHA (FIG. 2c). Peptide T was able to inhibit PHA stimulated PBMC cultures at a concentration of $1 \times 10^{-13}$M. Cultures stimulated with Con A or PWM were inhibited by as little as $1\times10^{-15}$M Peptide T. Peptide T reaches peak plasma concentrations of $5.5\times10^{-8}$M following administration in vivo; therefore, Peptide T mediated immunomodulation would be active at concentrations of the drug readily attainable in plasma and CSF. The culture medium, in which Peptide T was diluted, had no effect on lymphoproliferation. At the most effective concentration of Peptide T used, lymphoproliferation in response to PHA was inhibited 26%, PWM 38 and Con A 36%.

Figure 3:
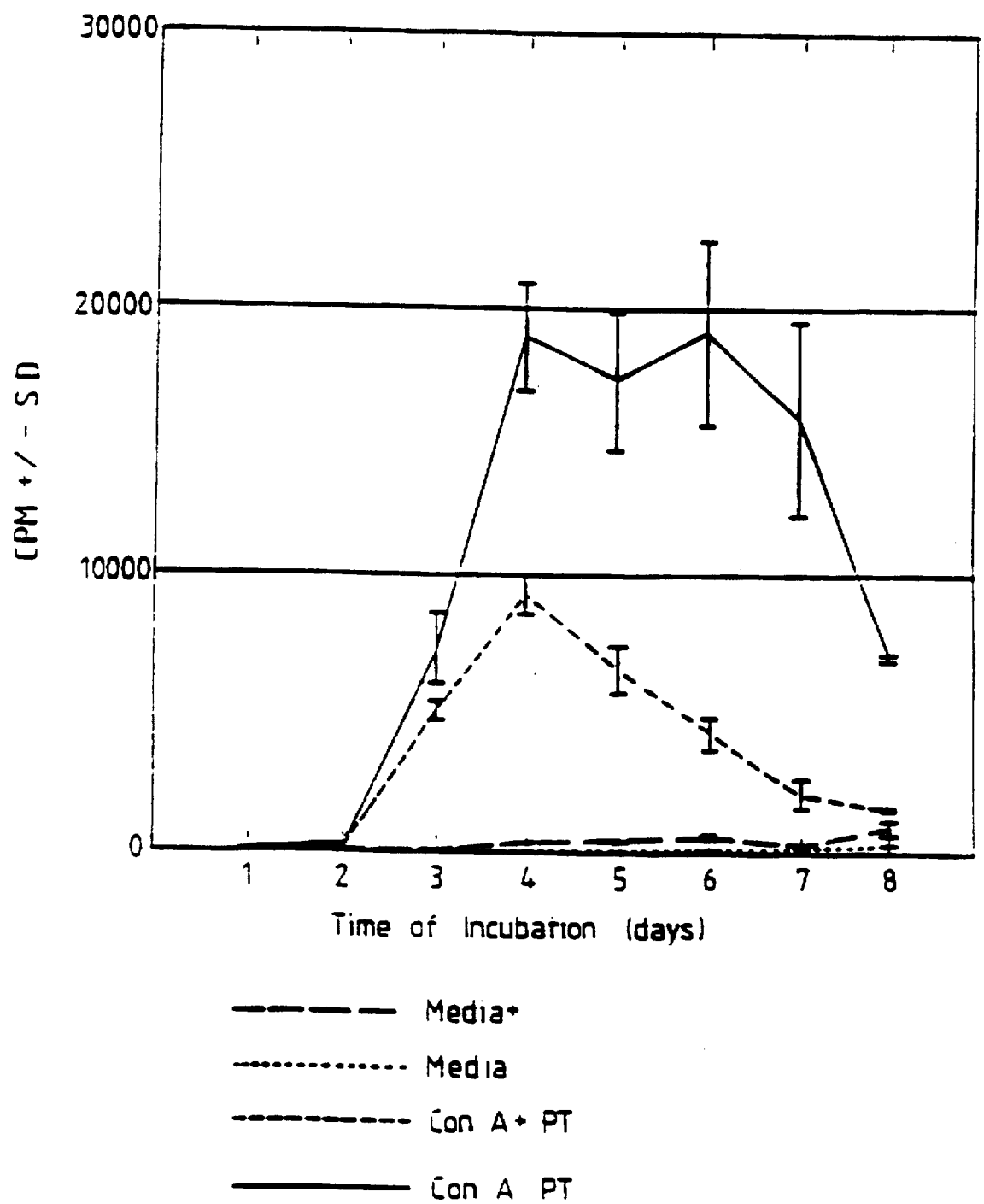

Inhibition of lymphoproliferation could be a result of cytotoxicity, a delay in initiation of proliferation, a reduction in growth rate or any combination of the above. When the Con A-induced proliferation of PBMC was measured daily, during the growth period (day 2–4) lymphocyte proliferation in the presence of Peptide T paralleled, but at a reduced rate, growth in the absence of the drug (FIG. 3). In the absence of mitogen, peptide T had negligible effects on PBMC. Therefore, Peptide T was not cytotoxic for responding lymphocytes nor did it delay the onset of proliferation. Peptide T allowed cells to grow, but at a reduced rate.

Peptide T was able to inhibit mitogen induced lymphoproliferation when added to PBMC after they had been exposed to mitogens (Table VII). This effect was present even when Peptide T was added three days after exposure of PBMC to mitogen. Peptide T mediated inhibition of lymphoproliferation was most pronounced when added to cultures that had been stimulated with Con A.

In addition to inhibition of lymphoproliferation, the presence of Peptide T reduced the amount of TNFα secreted into the supernatant (SN) of a 48 hour Con A stimulated culture of PBMC (Table VIII). Neither Peptide T nor RPMI had any reactivity in the RIA for TNFα. In the absence of Con A, no TNFα was detected in the culture supernatant.

TABLE VIII

PBMC ($5 \times 10^6$ PBMC/ml) were cultured for 48 hours in the presence or absence of Con A (6.25 µg/ml) = Peptide T ($10^{-9}$M, added concurrently with mitogen). Levels of TNFα in culture supernatants were determined as described.

| | TNFα (fmol/100 ul) |
|---|---|
| RPMI + Peptide T | <1 |
| PBMC + RPMI + Peptide T | <1 |
| PBMC + Con A | 69.0 ± 6.9 |
| PBMC + Con A + Peptide T | 47.0 ± 0.1 |

EXAMPLE 18

PEPTIDE T INHIBITS NON-MITOGEN-INDUCED LYMPHOPROLIFERATION

In contrast to mitogens which induce lymphocyte proliferation signals by ligating MO/AMC and T cells via carbohydrate moieties on a variety of cell surface receptors, non-mitogen stimulated lymphoproliferation mediated by recall antigens, superantigens, antibodies to CD3 (anti-CD3 and allogeneic MHC molecules interact solely with the T cell antigen receptor/CD3 complex (TcR/CD3). In this respect, non-mitogen stimuli are more specific than mitogens.

Only those lymphocytes with TcR complementary to processed antigen epitopes will respond to recall antigens. Typically this represents a small fraction of the total lymphocyte pool. Reactions to allogeneic MHC, characterised by the mixed lymphocyte reaction (MLR) is mediated by recognition of foreign MHC Class II molecules by the TCR of responding cells (*Adv. Immunol.* 31 271 (1981)). Approximately 10% of T cells are alloreactive (*Lancet* 339 824 (1992)). Superantigens such as Staphylococcal enterotoxins A and B (SEA and SEB) and toxic shock syndrome toxin-1 (TSST-1) stimulate growth of approximately 20% of the T cell pool (*Sci. Am.* 266 92 (1992)) by interaction with defined $V_\beta$ segments of the TcR (Science 244 811 (1989)). Anti-CD3 is able to stimulate the growth of 100% of T cells independent of accessory cell function by ligating TcR/CD3 complexes directly.

Since mitogens represent an artificial, non-specific form of lymphocyte activation, the effect of Peptide T on lymphoproliferation in response to recall antigens, anti-CD3, superantigens and MLR was assessed. In addition, T cell effector functions and the growth of spontaneously proliferating malignant cell lines were examined in the presence of Peptide T.

Unless otherwise stated, experimental conditions were generally as described in Example 17.

Peptide T does not inhibit non-mitgoen induced lymphoproliferation

Figure 4:
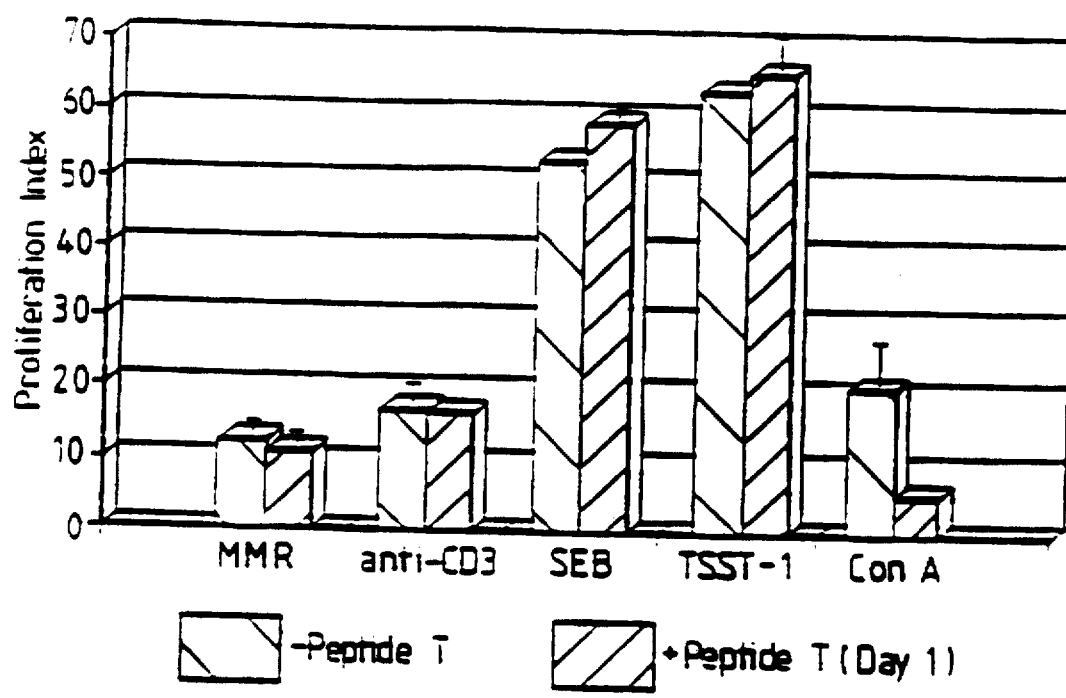
Figure 5:
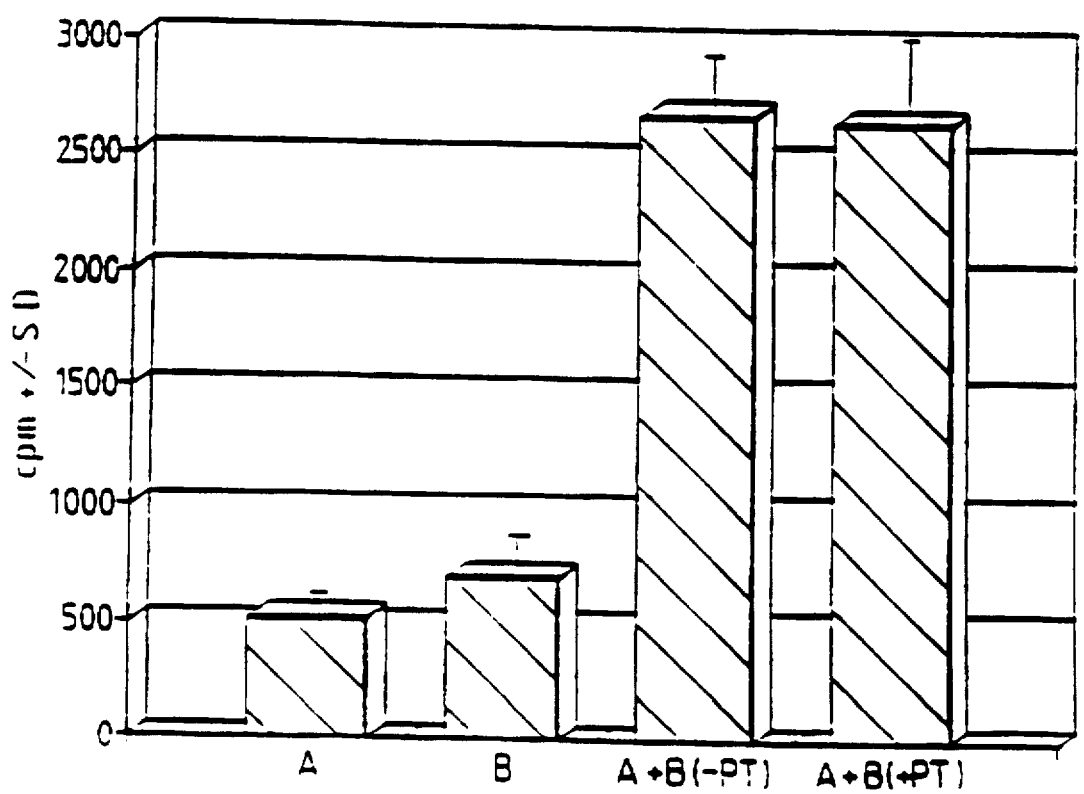

When added on the first day of a six day culture, Peptide T was able to inhibit Con A-induced lymphoproliferation, but had negligible effects on lymphocytes responding to recall antigen (measles, mumps, rubella vaccine, MMR), antibodies to CD3 or the superantigens SEB and TSST-1 (FIG. 4). Similarly, Peptide T did not affect the growth of lymphocytes in a mixed lymphocyte reaction (FIG. 5).

Molt-4 is a human T lymphoma cell line, p56$^{lck}$ negative, and Jurkat is a human T cell line, p56$^{lck}$ positive, that will grow spontaneously in the absence of exogenous stimuli. As the results of Table IX demonstrate, Peptide T did not significantly affect the growth of either Molt-4 or Jurkat cell lines.

TABLE IX

Effect of Peptide T on Growth of Cell Lines Two spontaneously growing human malignant T cell lines (Jurkat and Molt-4) were grown in the absence (Media − P.T.) or presence (Media + P.T.) of Peptide T added on the first day of culture. Growth was determined by measurement of incorporated $^3$H-thymidine; counters per minute (cpm) were not converted into a proliferation index. A higher cpm represents greater cell growth.

| | Media − P.T. (CPM ± S.D.) | Media + P.T. (CPM ± S.D.) |
|---|---|---|
| Jurkat | | |
| Day 1 | 7445 ± 261 | 8345 ± 131 |
| Day 2 | 14728 ± 1349 | 17441 ± 1360 |
| Day 3 | 41203 ± 6127 | 40002 ± 1572 |
| Day 4 | 50930 ± 1030 | 49852 ± 1011 |
| Day 5 | 80046 ± 1072 | 79748 ± 8474 |
| Day 6 | 109201 ± 8805 | 114967 ± 7342 |
| Day 8 | 113667 ± 7266 | 109144 ± 14052 |
| Molt-4 | | |
| Day 1 | 6182 ± 1296 | 6639 ± 726 |
| Day 2 | 13111 ± 370 | 15001 ± 1509 |
| Day 3 | 29175 ± 5594 | 32401 ± 850 |
| Day 4 | 39920 ± 3407 | 39839 ± 10740 |
| Day 5 | 54686 ± 1472 | 50269 ± 5436 |
| Day 6 | 56824 ± 3580 | 57370 ± 4968 |
| Day 8 | 10835 ± 264 | 19510 ± 4217 |

Peptide T does not inhibit PBMC mediated killing of Molt-4 cells

Figure 6:
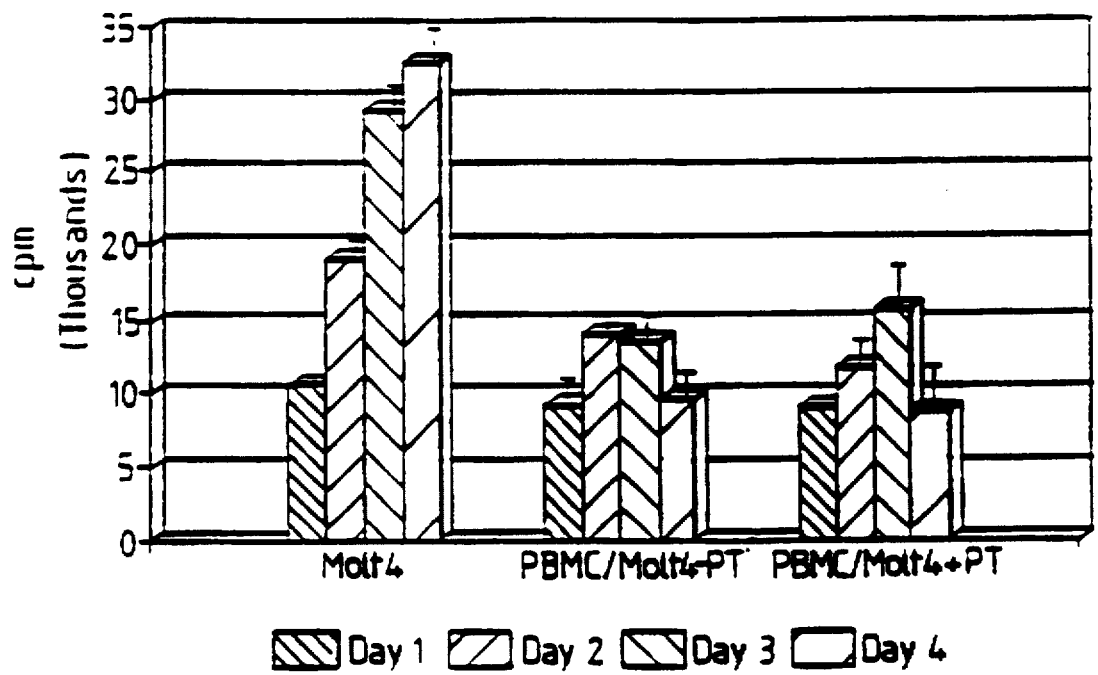

When PBMC are mixed with allogeneic Molt-4 cells the growth of Molt-4 is inhibited (FIG. 6). Alloreactive PBMC recognise Molt-4 as foreign and generate cytotoxic effector cells that kill Molt-4. Molt-4 is not a cytotoxic cell line and can not generate alloreactive effector cells. When Peptide T is added to this reaction, PBMC-mediated inhibition of Molt-4 proliferation remains unaffected (FIG. 6) suggesting that Peptide T does not affect the generation of cytotoxic effector functions. It is not possible to distinguish growth of alloreactive T cells from the growth of Molt-4 survivors since neither the growth of alloreactive T cells (FIG. 5) nor the growth of Molt-4 (Table IX) would be affected by Peptide T.

EXAMPLE 19

PEPTIDE T'S EFFECT ON MACROPHAGE AND TNF FUNCTION

Cells of the monocyte/macrophage lineage (MO/MAC) are long lived, non-proliferating cells that characterise chronic inflammatory reactions. MO/MAC function as non-specific phagocytes, antigen presenting cells (initiating antigen specific immune responses), as immunoregulatory cells and cytoxoxic effector cells. MO/MAC generate a variety of intracellular and extracelluar cytotoxic effector molecules including reactive oxygen intermediates, lysosomal enzymes and tumour necrosis factor alipha (TNF).

MO/MAC have been implicated in the pathogenesis of HIV disease. All MO/MAC express CD4 (*J. Immunol. Meth.* 135 59 (1990)) and are therefore capable of being infected with HIV. It has even been suggested that MO/MAC maybe the first cell to be infected with HIV during the infection process (*Annal. N.Y. Acid. Sci.* 616 1 (1990)). MO/MAC are not as susceptible to the cytopathic effects of HIV as are CD4 positive T cells (*TIPS* 12 28 (1991)) and may be responsible for the establishment of a persistent or latent HIV infection. MO/MAC may be responsible for transmission of HIV into the CNS where it comprises the primary cell type infected with HIV (*Compr. Ther.* 17 57 (1991)). In the CNS, MO/MAC may mediate neurological damage by releasing neurotoxic gp120 (*Science* 248 364 (1990)), tat (*J. Virol.* 65 961 (1991)) or MO/MAC derived neurotoxins (*Science* 250 1593 (1990)). It is interesting to note that activated MO/MAC have also been implicated in the pathogenesis of other neurological disorders such as multiple sclerosis (*Acta. Neuropathol.* 80 208 (1990); *Pathol. Immunopathol. Res.* 6 241 (1987); *Ann. Rev. Immunol.* 10 153 (1992)) and Alzheimer's disease (*Eur. Neurol.* 28 30 (1988)).

HIV-infected MO/MAC exhibit accessory cell dysfunction (*Clin. Immunol. Immunopathol.* 59 436 (1991); *J. Immunol.* 146 2297 (1991). In addition, HIV induces NO/MAC activation as indicated by enhanced levels of neopterin, a marker of T cell dependent MO/MAC activation, and enhanced levels of monokines (TNF, IL-1 and IL-6).

In vitro, MO/MAC may be activated by IFN-γ and lipopolysaccharide (LPS) which initiate at leat four distinct intracellular signals including a calcium flux (*Immunol. Today* 10 33 (1989)). The production of TNF may be initiated by IFN activation of MO/MAC but requires LPS to trigger its release (*J. Exp. Med.* 175 405 (1992)).

A role for TNF in HIV disease has been suggested based on the observations that macrophages from AIDS patients release grater amounts of TNF than those from normal controls (*Am. Rev. Respir. Dis.* 144 195 (1991)) and increased levels of TNF have been associated with progression from latent HIV infection to AIDS (*Am. J. Med.* 85 289 (1988)). Potential effects of TNF contributing to HIV pathogenesis include TNF mediated cachexia (New Eng. J. Med 327 329 (1992); *J. Nutr.* 122 749 (1992)), autocrine/paracrine enhancement of HIV replication (*Immunol. Today* 11 176 (1990)), hyperactivation of the immune system (*Biotherapy* 3 127 (1991)), inhibition of zidovudine (AZT), ddI and ddC (*VIII Int'l Conf. AIDS* Abst. #PoA 2326 (1992); *J. Intern. Med.* 228 549 (1990)), expansion of autoreactive CD4 specific CTL (*VIII Int'l Conf. AIDS* Abst.#PoA 2365 (1992)), damage to myelin and oligodendrocytes (*AIDS* 5 1405 (1991)), cytopenia (*Am. Rev. Respir. Dis.* 144 195 (1991) and apoptosis (*Immunol. Ser.* 56 315 (1992)).

TNF has also been implicated in the pathogenesis of multiple sclerosis. TNF is cytotoxic for myelin producing oligodendrocytes (*Ann. Rev. Immunol.* 10 153 (1992)) and can cause myelin damage directly by inducing blebbing and swelling of the myelin sheath (*Annal. Neurol.* 23 339 (1988)).

Methods

Macrophage Cytotoxicity Assay

The MO/MAC cytotoxicity assay is a two step assay. After isolation of adherent cells (mainly MO/MAC) from PBMC, MO/MAC are activated by lymphokines (including IFN gamma and LPS. Subsequent to washing which removes activators, $^3$H-thymidine labelled K562 target cells were added to activated MO/MAC and incubated for 3 days. The degree of cytotoxicity was proportional to the amount of radioactive label released into the culture supernatant, is shown in the following scheme:

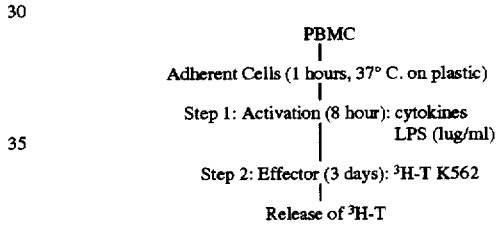

MO/MAC Supernatant Cytotoxicity

Supernatant (SN) of activated MO/MAC were collected from monolayers of PBMC derived adherent cells that had been exposed to LPS for 23 hours. This SN was tested for cytolytic activity against $^3$H-thymidine labelled K562 cells in a 48 hour, 37° C. cytotoxicity assay. SN were stored at 4° C. overnight or stored frozen at -20° C. for longer periods before using.

Results

Peptide T inhibits MO/MAC mediated cytotoxicity

Figure 7:
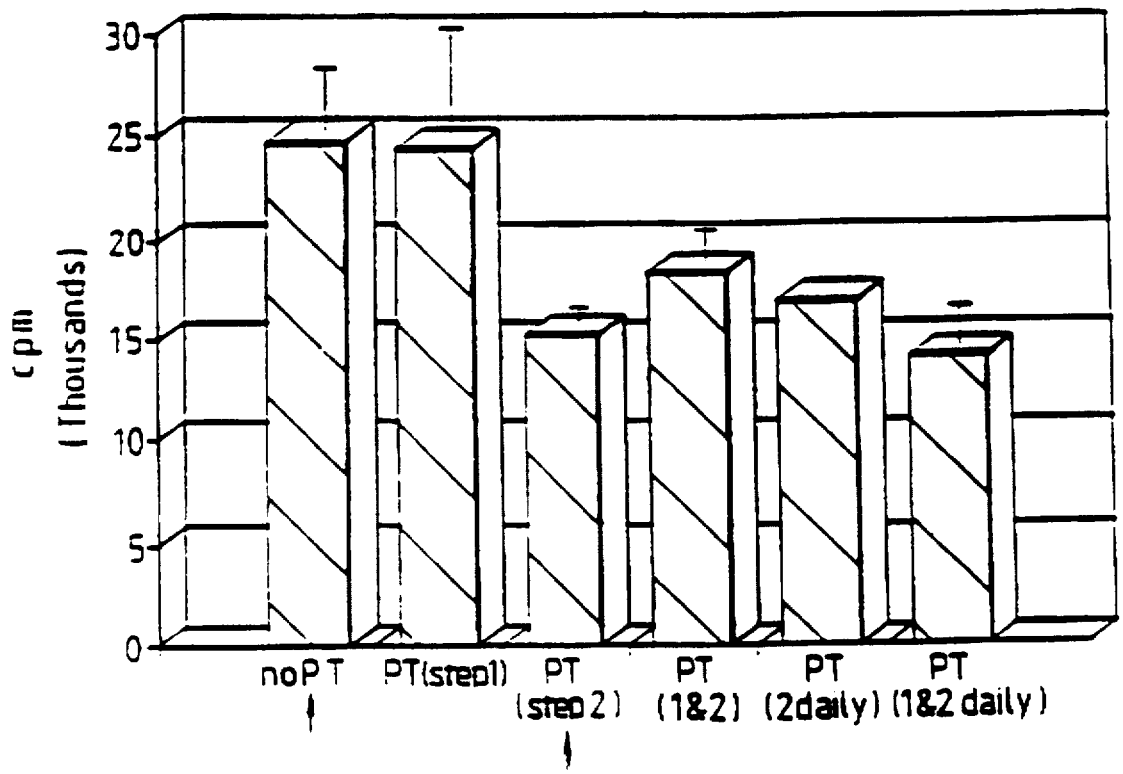

The presence of Peptide T at different stages of the cytotoxicty assay demonstrated that while Peptide T did not affect the ability of resting MO/MAC to be activated, it was able to inhibit the cytotoxicity of activated MO/MAC (FIG. 7). Whether Peptide T was added concurrently with target cells or every day of the culture did not affect the drug's activity.

Peptide T treatment reduces neopterin levels but Peptide T-dependent decreases in serum neopterin were not associated with decreases in serum IL-1. When sera from patients with Peptide T dependent decreases in elevated neopterin levels were tested for IL-1, no correlation between the two could be demonstrated (Table X). However, neopterin levels were elevated prior to Peptide T administration whereas serum IL-1 levels were normal.

TABLE X

Serum IL-1 and Neopterin Concentration Serum was collected from patients with HIV disease and stored at −20° C. Neopterin and IL-1 concentrations were determined by RIA. Pre- and post-Peptide T values of IL-1 and neopterin were determined for the same serum samples.

| PAT- | [IL-1] (fmol/100 µl) | | [Neopterin] (nM) | |
|---|---|---|---|---|
| IENT | pre-Peptide T | post-Peptide T | Pre-Peptide T | post-Peptide T |
| norm. | 4 ± 0.03 | N/A | ND | ND |
| BL | 4.1 ± 0.03 | 4.7 ± 0.05 | ND | ND |
| CJ | 3.7 ± 0.03 | 4.2 ± 0.02 | ND | ND |
| TS | 4.2 ± 0.14 | 4.2 ± 0.26 | ND | ND |
| LB | 3.9 ± 0.13 | 4.35 ± 0.003 | ND | ND |
| BG | 4.35 ± 0.06 | 4.6 ± 0.02 | 52.0 ± 4.0 | 16.85 ± 0.05 |
| BC | 3.5 ± 0.14 | 3.8 ± 0.12 | 47.3 ± 0.8 | 32.5 ± 3.5 |
| JM | 5.23 ± 0.17 | 4.2 ± 0.07 | 27.8 ± 0.8 | 19.75 ± 0.25 |
| RH | 4.1 ± 0.01 | 4.6 ± 0.11 | 13.15 ± 2.85 | 8.9 ± 0.6 |

Peptide T inhibits cytotoxicity of MO/MAC culture supernatants.

Figure 8:
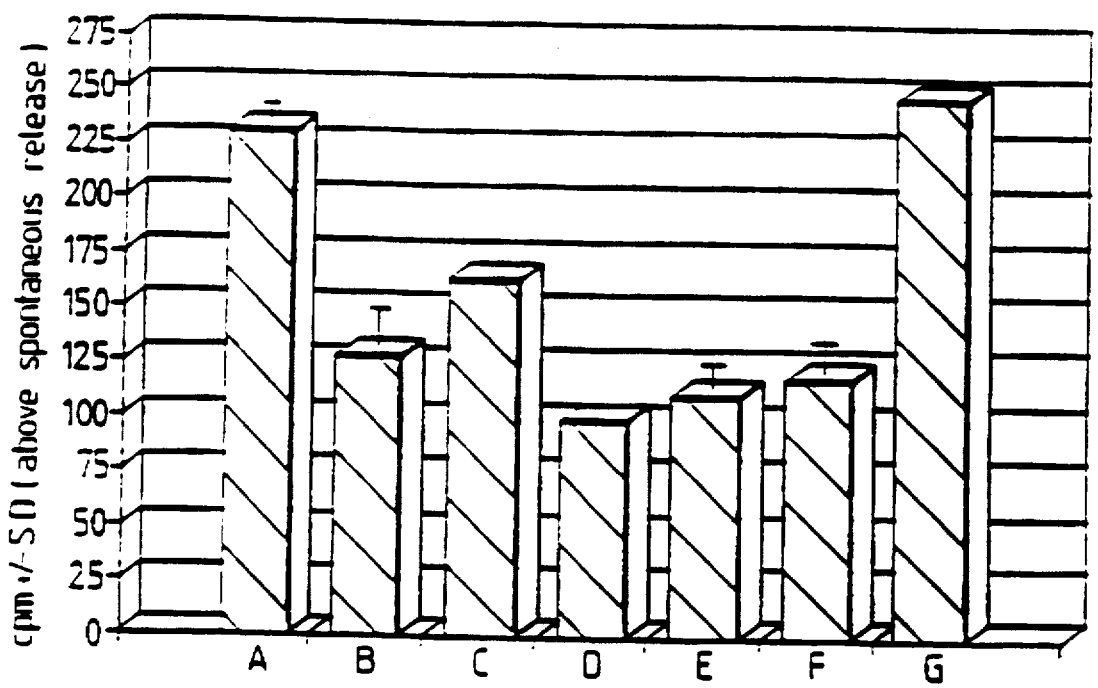
Figure 9:
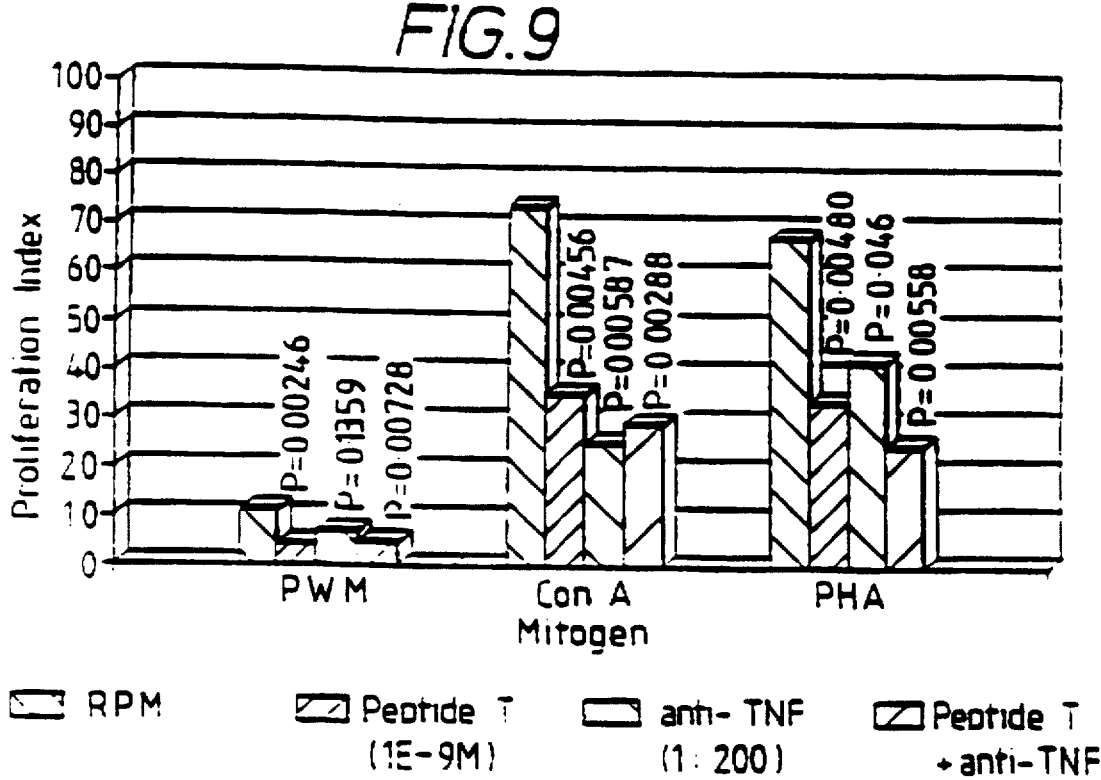

The ability of MO/MAC culture SN to lyse target K562 cells was determined in the presence of Peptide T. MO/MAC culture SN was used at a final dilution of 1:6 in the culture well. As shown in FIG. 8, Peptide T was able to block MO/MAC SN mediated lysis of K562 even when added at $1 \times 10^{-13}$M.

EXAMPLE 20

PEPTIDE T HAS A SIMILAR EFFECT TO ANTI-TINE IN INHIBITING THE EFFECTS OF TNF $10^5$ PBMC were cultured in the presence of PWM, Con A or PHA (see Example 17). Peptide T ($10^{-9}$M), anti-TNF MoAb #47 at a 1:200 dilution (antiTNF) or a combination of them both were added to cultures concurrently with mitogens. Following a five day incubation, cultures were pulsed with $^3$H-thymidine 18–24 hours prior to harvesting. Incorporated $^3$H-thymidine was converted to a proliferation index (see Example 17). Data were analysed by two sample ANOVA using 95% confidence limits.

EXAMPLE 21

PEPTIDE T DECREASES SERUM TNF LEVELS IN HIV PATIENTS

Figure 10:
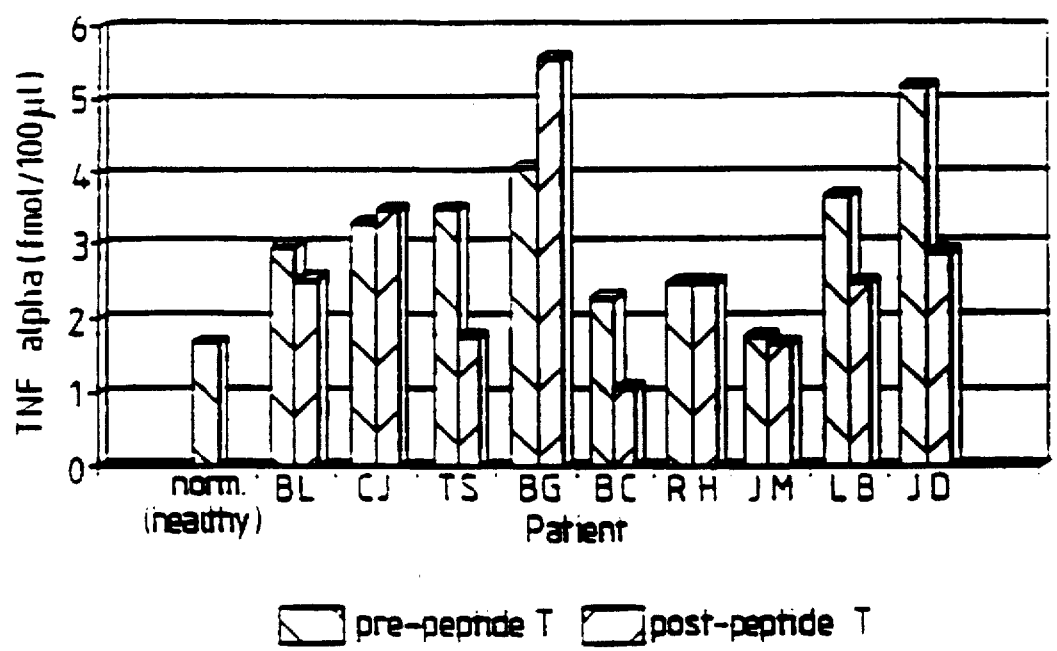
FIG. 10 is referred to in Example 21 and shows that Peptide T decreases serum TNF levels in HIV patients.

Serum levels of TNF were determined in patients with stage IV HIV disease pre- and post-Peptide T treatment. Patients had been receiving drug from 2 weeks to 11 months. Results are shown in FIG. 10. The increase in serum TNF levels in patient BG was associated with the development of an opportunistic infection.

EXAMPLE 22

PEPTIDE T PROLONGS SURVIVAL D-GALACTOSAMINE-SENSITIZED MICE IN A SEPTIC SHOCK MODEL

Fifty BALB/c/Swiss (1st cross) female mice approximately 8 weeks old were split into five groups and dosed as follows:

1. 16 mg D-galactosamine+20 µg TNF+H$_2$O
2. 16 mg D-galactosamine+20 µg TNF+MAb 47
3. 16 mg D-galactosamine+20 µg TNF+100 µg Peptide T
4. 16 mg D-galactosamine+20 µg TNF+1 µg Peptide T
5. 16 mg D-galactosamine+20 µg TNF+1 µg Peptide T D-galactosamine sensitizes the mice to the effects of TNF in this experimental septic shock model. MAb 47 is a broad spectrum anti-TNF monoclonal antibody available from Peptide Technology Limited.

The protective effect of Peptide T was assessed after 12 hours. The results in the following Table XI were obtained.

TABLE XI

| | A | B | C | D | E | F | G | H | Alive | Dose |
|---|---|---|---|---|---|---|---|---|---|---|
| 1 | 0 | 0 | 0 | 0 | 0 | 0 | 0 | 0 | 0 | TNF |
| 2 | 0 | 4 | 10 | 4 | 2 | 3 | 6 | 10 | 14 | TNF + <An |
| 3 | 0 | 1 | 8 | 1 | 1 | 1 | 2 | 8 | 9 | TNF + 100 µg PT |
| 4 | 1 | 1 | 5 | 3 | 1 | 1 | 0 | 5 | 7 | TNF + 10 µg PT |
| 5 | 1 | 1 | 2 | 2 | 1 | 0 | 0 | 1 | 4 | TNF + 1 µg PT |

Parameters:
A Cold
B Cool
C Warm
D Ruffled
E Diarrhoea
F Discharge from Eyes
G Touch Sensitive
H Activity

EXAMPLE 23

D-Thr-Thr-Tyr-D-Thr-NH$_2$ PROLONGS SURVIVAL OF SENSITISED MICE ADMINISTERED A LETHAL DOSE OF LPS

Meth A ascites tumour cells were injected ($10^6$ cells i.p.) into mice and allowed to grow. The Meth A tumour-bearing mice were thereby sensitized to the effects of TNF/LPS. The mice were administered with 50 µg LPS, formulated in phosphate-buffered saline (PBS), by injection i.p. and divided into three groups of ten. Treatment of each group was then as follows:

1. Positive control. 1 mg polymyxin B (PMB) in PBS injected i.p. (PMB is an inhibitor of LPS activity.)
2. Negative control. PBS injected i.p.
3. Compound under test. 1 mg Peptide T analogue 623 (D-Thr-Thr-Tyr-D-Thr-NH$_2$) in PBS injected i.p.

Figure 11:
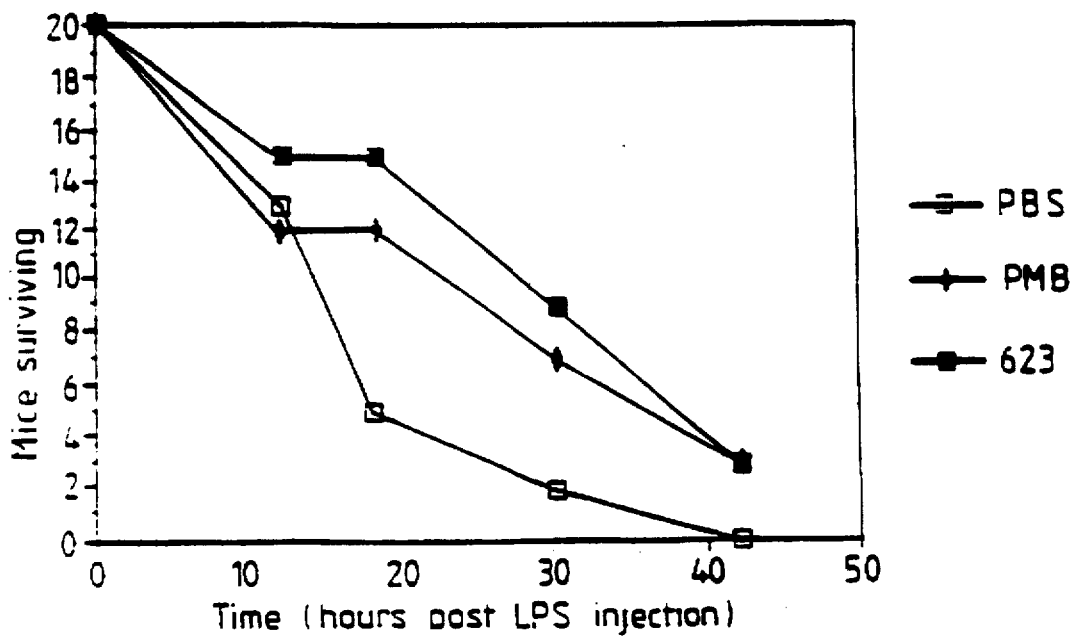
FIG. 11 is referred to in Example 23 and shows that Peptide T analogue 623 prolongs survival of sensitised mice administered a lethal dose of LPS.

The results are shown in FIG. 11. Survival of the mice treated with analogue 623 was at least a good as that of PMB-treated mice.

EXAMPLE 24

PEPTIDE T INHIBITS ACTIVATION OF HUMAN NEUTROPHILS BY TNF AND LPS

Neutrophils. Neutrophils were isolated from whole blood from healthy blood donors. Separation was achieved by the rapid-single-step method of centrifugation of whole blood on FICOLL-HYPAQUE™. These were >99% viable and usually >98% pure.

Peptides and TNF. TNF was a recombinant product produced in *E. coli*. Peptide T and analogue 505 (D-Ser-Ser-D-Thr-Thr-D-Thr-Thr-Tyr-D-Thr) were resuspended in Hank's Balanced Salt Solution (HBSS).

Figure 12:
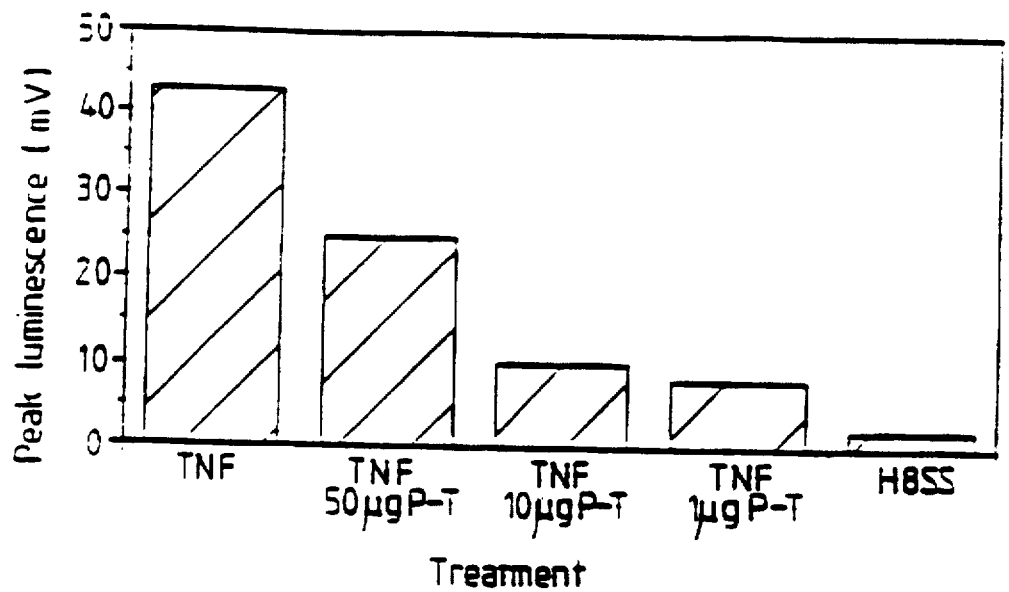
FIG. 12 is referred to in Example 24 and shows that Peptide T inhibits activation of human neutrophils by TNF.
Figure 13:
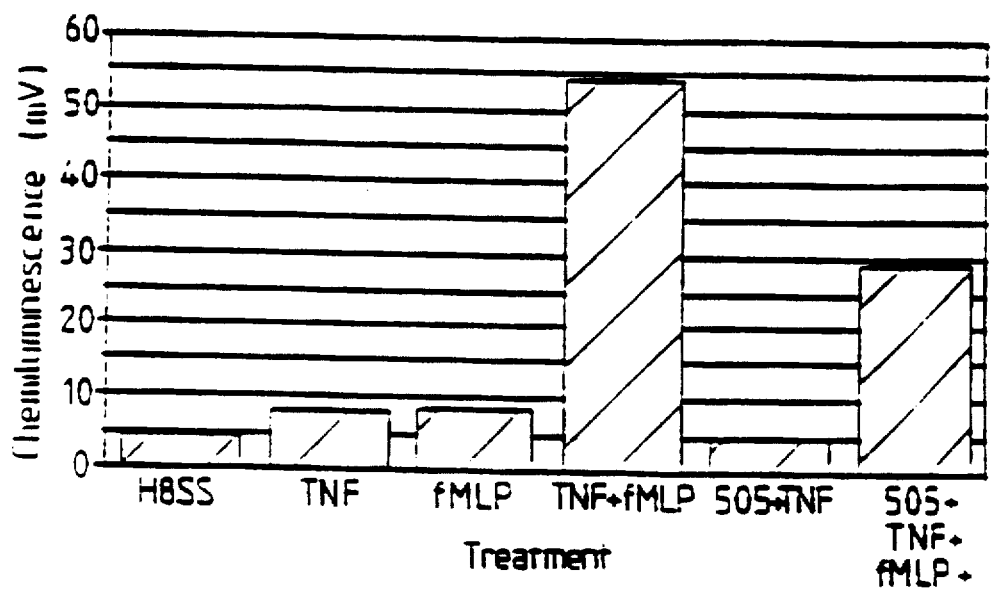
FIG. 13 is also referred to in Example 24 and shows that Peptide T analogue 505 inhibits TNF priming and activation of human neutrophils.
Figure 14:
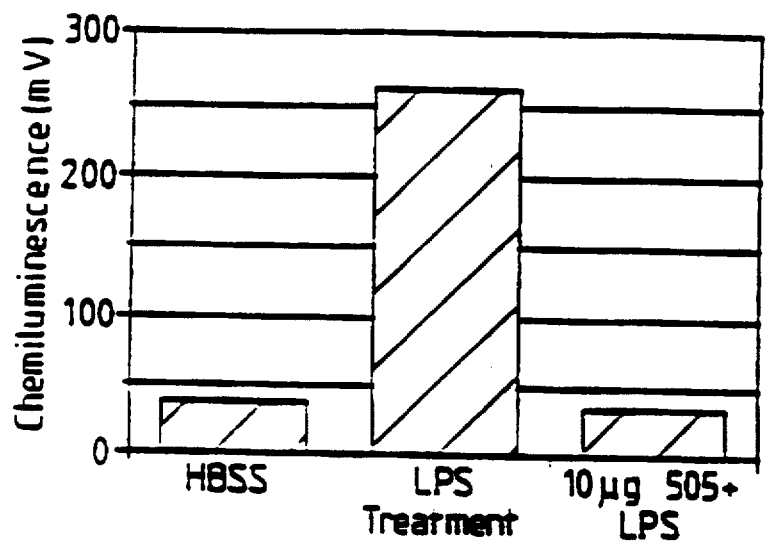
FIG. 14 is again referred to in Example 24 and shows that Peptide T analogue 505 inhibits LPS activation of human neutrophils.

Examination of Peptide T's and analogue 505's effect on stimuli-induced neutrophil (100 µg) by chemiluminescence. To 100 µl of 500–1000U/ml of TNF was added 10 µl of peptide and after 5 min 100 µl of $1 \times 10^7$ neutrophils/ml was added. The cells further incubated at 37° C./20 min and then tested for chemiluminescence activity. In some cases an agonist such as fMLP ($10^{-7}$M) was added. Chemiluminescence was measured in a luminometer (LKB). The results for Peptide T are presented in FIG. 12 as peak rate of CL release. Lucigenin-dependent chemiluminescence was measured: this represents superoxide measurement. In another set of experiments the effects of analogue 505 on the LPS-induced neutrophil chemiluminescence were examined. In this case the LPS was essentially substituted for the TNF. The concentration of LPS was 0.005 µg/ml. The results are presented in FIGS. 13 and 14, which show respectively that analogue 505 (a) inhibits TNF priming and activation of human neutrophils and (b) inhibits LPS activation of human neutrophils.

EXAMPLE 25

PEPTIDE T REDUCES TNF-MEDIATED PROTEOGLYCAN DEGRADATION AND REDUCES TNF'S ABILITY TO STIMULATE NEUTROPHIL-MEDIATED DEGRADATION OF CARTILAGE (a) In one group of experiments various concentrations of peptide T were mixed with TNF and then added to $^{35}$S-labelled cartilage. The cartilage was cultured for 3 days at 37° C. and on each day the supernatant was removed to determine the amount of degradation. The cartilage culture was replenished daily with TNF or peptide T-TNF.

(b) In another group of experiments the human neutrophils was treated with TNF or peptide T-TNF and then added to cartilage. The neutrophil mediated cartilage degradation determined.

RESULTS

1. Effects of peptide T on TNF-induced cartilage degradation

TABLE XII

Effect of peptide T on TNF-induced cartilage proteoglycan degradation

| Cartilage treatment | % Cumulative release (day 1, 2, 3) | |
|---|---|---|
| | Exp 1 | Exp 2 |
| TNF* | 45.5 | 23.1 |
| TNF + 1 µg peptide T | 11.1 | −0.5 |
| TNF + 10 µg peptide T | 3.2 | 1.7 |
| TNF + 100 µg peptide T | 15.9 | 13.2 |

*100 U of TNF

2. Effects of peptide T on TNF-primed neutrophil for proteoglycan degradation

Peptide T reduced the ability of TNF to stimulate neutrophil-mediated degradation of cartilage (Table XIII).

TABLE XIII

The effect of peptide T on TNF priming of neutrophils for cartilage damage

| Treatment of neutrophils | % Cumulative release | | |
|---|---|---|---|
| | Exp 1 | Exp 2 | Exp 3 |
| TNF* | 17.4 | 6.8 | 5.3 |
| TNF + 10 µg peptide T | −5.2 | 9.9 | 1.9 |
| TNF + 100 µg peptide T | −0.8 | 0.9 | 0.6 |

*100 U or TNF

This example effectively gives good in vitro support to the anecdotal clinical evidence presented in Examples 13 and 14.

EXAMPLE 26

PEPTIDE T REDUCES TISSUE FACTOR EXPRESSION INDUCED BY TNF

In acute systemic inflammation, for example in a septic shock patient, disseminated intravascular coagulation can be observed. During the course of the coagulation reaction, endothelial cells are involved as mediators of cell adhesion. One factor which is produced and which is involved in the coagulation cascade is tissue factor, also known an endothelial cell procoagulant activity; it is induced by TNF. In this example, it is demonstrated that Peptide T inhibits tissue factor expression by endothelial cells, thereby showing that Peptide T inhibits some of the pathology associated with acute inflammatory reactions.

Figure 15:
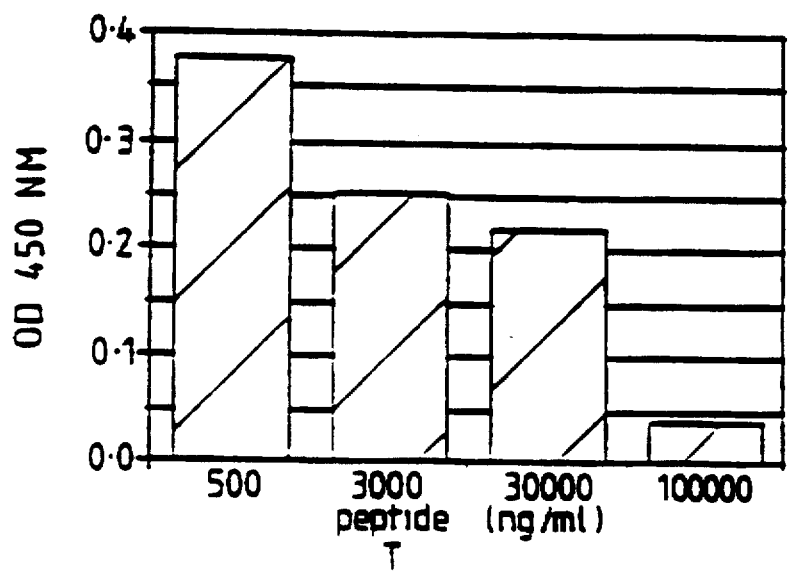
FIG. 15 is referred to in Example 26 and shows that Peptide T reduces TNF-induced expression of tissue factor in HUVECs.

Methodology Human umbilical vein endothelial cells were cultured essentially by the method of Bevilacqua et al. *Proc. Natl. Acad. Sci. USA* 83 4533–4537 (1986). Cell cultures were treated with TNFα at 3 µg/ml for 4 hours at 37° the presence or absence of Peptide T. Tissue factor expression was measured by an ELISA, following absorbence at 450 nm. The results are shown in FIG. 15, from which it can be seen that increasing concentrations of Peptide T progressively reduce tissue factor expression.

EXAMPLE 27

HEALTH-RELATED QUALITY OF LIFE AND SYMPTOM ASSESSMENT IN MS PATIENTS

To evaluate the impact of drug-related change on overall health and symptom burden, MS patients were followed routinely with both recognized and newly developed health-related quality of lift instruments: an MS-modified version of the 30-item Medical Outcomes Study-HIV Survey (MOS-HIV) originally developed by Dr. Albert Wu, the 22-item Psychological General Well-Being Schedule (PGWB) developed by Dr. Harold Dupuy, and the MS Symptom Checklist developed for this study. These instruments, of which the first two have previously been validated and shown to be responsive to change in other disease states, allow quantitation of self-reported symptom variation (see Brook et al., *Medical Care* 17 (7 Suppl.) 1–54 (1979), Fazio "A Concurrent Validation Survey of the NCHS General Well-Being Schedule", US Dept of Health, Education and Welfare, National Center for Health Statistics, Hyattsville, Md., USA 1977, McDowell and Newell "Measuring Health: A Guide to Rating Scales and Questionnaires", Oxford University Press 1987, Stewart et al., *Medical Care* 26 724–35 (1988), *JAMA* 262 907–13 (1989), and "Measuring Functioning and Well-Being of Patients with Chronic Conditions: The Medical Outcomes Study Approach", Duke University Press 1992, Wachtel et al., *Ann. Int. Med.* 116 129–1367 (1992), Ware et al., "conceptualization and Measurement of Health for Adults in the Health Insurance Survey, Vol III; Mental Health", Rand Corporation 1979, and We et al., *Medical Care* 29(8) 786–98 (1991).

Given the small number of patients involved in this report, some of whom received Peptide T in an on-off-on design, it would not be expected that statistical significance might be obtained. To facilitate establishment of any trends, three patients who stopped taking Peptide T and then restarted the drug some weeks later after a new baseline period appear twice in the following analysis. In this manner, 8 baseline and repeated measures (at weeks 0, 4, 8, and 12) were defined and analysed using two-tailed paired t-tests: see Table XIV.

TABLE XIV

Two-tailed Paired T-Tests, MS Patients
Note: Starts and re-starts after washout are considered as separate examples.
In all scales, a higher score indicates improvement.

| ITEM | BASELINE | | Week 4 | | | Week 8 | | | Week 12 | | |
|---|---|---|---|---|---|---|---|---|---|---|---|
| MOS-HIV | n = 8 | | n = 8 | | | n = 6 | | | n = 5 | | |
| (all scored 0–100) | Mean | SD | Mean | SD | P-value | Mean | SD | P-value | Mean | SD | P-value |
| Discomfort | 30 | 15.1 | 55 | 25.6 | .019 | 60 | 25.3 | .082 | 52 | 30.3 | .109 |
| Mental Health | 58.5 | 21.4 | 72.5 | 9.7 | .102 | 81.3 | 10 | .125 | 76.8 | 11.8 | .07 |
| Energy | 35.6 | 19.4 | 63.8 | 12.2 | .005 | 69.2 | 13.6 | .006 | 67 | 14.4 | .031 |
| Health Distress | 69.4 | 28.5 | 89.4 | 9 | .078 | 95.8 | 4.9 | .1 | 89 | 14.7 | .086 |
| Quality of life | 53.12 | 16 | 81.25 | 11.6 | .007 | 83.3 | 12.9 | .012 | 75 | 17.7 | .016 |
| Well-Being | 49.3 | 17.25 | 72.4 | 9.3 | .006 | 77.9 | 9.3 | .023 | 72 | 14.3 | .013 |
| MOS Summary | 47.7 | 19.8 | 61.9 | 14.5 | .003 | 69.7 | 14.4 | .003 | 71.5 | 15.6 | .015 |
| | n = 7 | | n = 7 | | | n = 5 | | | n = 5 | | |
| PGWB | MEAN | SD | MEAN | SD | P-value | MEAN | SD | P-value | MEAN | SD | P-value |
| Vitality (0–20) | 9.1 | 3.3 | 15 | 2.6 | .003 | 14.8 | 1.6 | .03 | 15 | 2.1 | .011 |
| PGWB Summary (0–110) | 63.5 | 13.2 | 79.8 | 7.5 | .007 | 85.8 | 10.7 | .003 | 81 | 13.3 | .009 |
| | n = 7 | | n = 7 | | | n = 6 | | | n = 6 | | |
| SYMPTOM CHECKLIST | MEAN | SD | MEAN | SD | P-value | MEAN | SD | P-value | MEAN | SD | P-value |
| Fatigue (0–4) | 1.375 | 0.916 | 2.86 | 0.9 | .025 | 3.17 | 0.75 | .001 | 3.33 | 0.52 | .007 |
| Malaise (0–4) | 2.29 | 1.1 | 3.33 | 0.52 | .042 | 3.83 | 0.41 | .025 | 3.4 | 0.55 | .14 |
| Forgetfulness (0–4) | 3 | 1.1 | 3.6 | 0.53 | .046 | 3.7 | 0.52 | .101 | 3.83 | 0.41 | .101 |
| Slow thinking (0–4) | 2.88 | 0.99 | 3.43 | 0.79 | .103 | 3.67 | 0.52 | .042 | 3.83 | 0.41 | .042 |

In the MS-modified MOS_HIV, either a trend or statistically significant improvement was observed at weeks 4, 8, and 12 even in this small sample in such dimensions of health as physical discomfort, mental health, and health distress. Improvement was statistically significant at all three measurement points in energy, general quality of life, well-being and the unweighted summary score. General overall improvement was corroborated by the summary scope of the PGWB.

Remarkable improvement in energy was corroborated by the vitality subscale of the PGWB and by ratings of the impart of fatigue on daily activities.

Improvement in malaise was statistacally significant at 4 and 8 weeks. In regard to neurocognitive manifestations of MS, there was a trend towards improvement in forgetfulness and slowness in thinking.

In health related quality of life assessment, a statistically significant change of greater than 0.5 standard deviations is usually taken as indication of moderate clinically significant change (see Testa, J. Hypertension 5 S9–S13 (1987)). All improvements noted above easily exceeded this test, with many improvements being greater than 1 standard deviation. Mean improvements in measures of energy at week 12 on all three instruments exceeded 2 standard deviations, an indication of very great clinical change in a common and debilitating symptom of MS.

These quantifiable assessments over time support the clinical observations of significant improvement.

We claim:

1. A method of treating inflammatory bowel disease in patients in need of such treatment by administering an effective amount of: I-A-B-C-D-E-F-G-H-II (General Formula 1)

wherein A is Ala, Gly, Val, Ser, Thr or absent,
B is Ala, Gly, Val, Ser, Thr, or absent,
C is Ser, Thr or absent,
D is Ser, Thr, Asn, Glu, Arg, Ile, Leu or absent,
E is Ser, Thr, Asp or absent,
F is Ser, Thr, Asp or absent,
G is Tyr or absent,
H is Thr, Arg, Gly, Met, Met(O), Cys, Thr, Gly or absent and I is Cys or absent
II is Cys, an amide group, substituted amid group, an ester group or absent.

at least one of the amino acids optionally being substituted by a monomeric or polymeric carbonhydrate or derivative thereof, such substitution being accomplished through hydroxyl and/or amino and/or amido groups of the amino acids, and wherein the peptide comprises at least 4 amino acid residues, or a pharmaceutically acceptable salt thereof.

2. The method in accordance with claim 1 wherein tetra-, penta-, hexa-, hepta-, octa- or nonapeptide are administered wherein one or more amino acid(s), is/are deletered from either the carboxy or amino terminal, and where the carboxy terminal amino acid can be in the form of an amide, substituted amide or an ester.

3. The method in accordance with claim 1, wherein at least one of the hydroxyl groups on a Ser, Thr or Tyr residue is derivatised into an ester or ether compound.

4. The method in accordance with claim 1, wherein at least one of the amino acids is a substituted N-lkyl amino acid.

5. The method in accordance with claim 1, wherein at least one of the amino acids is substituted with a monomeric or polymeric carbonhydrate, or a derivative thereof, the substitution(s) being accomplished through hydroxyl- and/ or amino-groups of the amino acids.

6. The method in accordance with claim 1, wherein the peptide comprises the amono acid sequence
-Thr-Thr-Asn-Try-Thr-.

7. The method in accordance with claim 1, wherein the peptide is

1. D-Ala-Ser-Thr-Thr-Thr-Asn-Try-Thr-NH$_2$;

2. Ala-Ser-Thr-Thr-Thr-Asn-Tyr-Thr;

3. D-Ala-Ser-Thr-Thr-Thr-Asn-Tyr-Thr;

4. D-Ala-Ala-Ser-Ser-Ser-Asn-Tyr-Met;

5. Thr-Asp-Asn-Try-Thr;

6. Thr-Thr-Ser-Tyr-Thr;

7. Thr-Thr-Asn-Tyr-Thr;

8. D-Thr-Thr-Tyr-D-Thr;

9. D-Ala-Ser-D-Thr-Thr-D-Thr-Asn-Tyr-D-Thr-NH$_2$;

10. D-Ser-Ser-D-Thr-Thr-D-Thr-Thr-Tyr-D-Thr-NH$_2$; or a derivative or salt thereof.

8. The method in accordance with claim 1, wherein the peptide is D-Ala-Ser-Thr-Thr-Thr-Asn-Tyr-Thr-NH$_2$, or a derivative or salt thereof.

9. The method in accordance with claim 1, wherein the method comprising administering to a subject an effective amount of a peptide to treat inflammatory bowel disease.

10. The method in accordance with claim 1, wherein the effective amount comprises from 0.05 to 10000 mg of peptide per day.

11. The method in accordance with claim 1, wherein the effective amount comprises 0.5–1000 mg of peptide per day.

12. The method in accordance of claim 1, wherein the effective amount comprises 5–100 mg of peptide per day.

13. The method in accordance with claim 1, wherein the peptide is administered in a pharmaceutical composition in association with a pharmaceutically acceptable carrier.

14. The method in accordance with claim 1, wherein the pharmaceutically acceptable carrier is selected from carriers which adapt the composition for intranasal, oral, buccal, parenteral, topical or rectal administration or for direct inhalation.

15. The method in accordance with claim 1, wherein the carrier provides the peptide in solution, suspension, emulsion or gel.

16. The method in accordance with claim 1, wherein the peptide is provided in lyophilised form.

17. The method in accordance with claim 1, wherein the composition includes a formulating agent which is a suspending agent and/or stabilising agent and/or a dispersing agent.

18. The method in accordance with claim 1, when a peptide is conjugated to a peptide, protein or other appropriate carrier and/or an excipient.

* * * * *

UNITED STATES PATENT AND TRADEMARK OFFICE
CERTIFICATE OF CORRECTION

PATENT NO. : 5,756,449
DATED : May 26, 1998
INVENTOR(S) : Anders Jorgen Andersen, et al.

It is certified that error appears in the above-identified patent and that said Letters Patent is hereby corrected as shown below:

Column 6, line 62 reads "*enterol.* 25 (Supp. 175) 97-106 (1990); Pepperscorn, *Annal.*" and should read --*enterol.* 25 (Supp. 175) 97-106 (1990); Peppercorn, *Annal.*--

Column 7, line 19 reads "inflammatory response in number of diseases. These" and should read --inflammatory response in a number of diseases. These--

Column 9, line 26 reads "Thr-Thr-Thr-Thr-Asn-Tyr-Thr-amide (SEQ ID NO:3)." and should read --Thr-Thr-Thr-Asn-Tyr-Thr-amide (SEQ ID NO:3).--

Column 9, line 65 reads "terminal amino acid as a D-stereoisomeric, to protect the" and should read --terminal amino acid as a D-stereoisomer, to protect the--

Column 10, line 55 reads "F is Thr, Ser, Asn, Gln, Lys, Trp or absent," and should read --F is Thr, Ser, Asn, Arg, Gln, Lys, Trp or absent,--

Column 11, line 20 reads "neoplstic agent." and should read --neoplastic agent.--

Column 11, line 27 reads "intramuscular, intravenous, intra-articular or intr-cisternal" and should read --intramuscular, intravenous, intra-articular or intra-cisternal--

Column 13, line 61 reads "VIP (66, 66, 68, 69: TDNYT) and the core peptide" and should read --VIP (66, 67, 68, 69: TDNYT) and the core peptide--

Column 13, line 62 reads "(61-65; TTNYT) share the nomologous sequence that binds" and should read --(61-65: TTNYT) share the nomologous sequence that binds--

UNITED STATES PATENT AND TRADEMARK OFFICE
CERTIFICATE OF CORRECTION

PATENT NO. : 5,756,449

DATED : May 26, 1998

INVENTOR(S) : Anders Jorgen Andersen, et al.

It is certified that error appears in the above-identified patent and that said Letters Patent is hereby corrected as shown below:

Column 16, line 31 reads "tide T parallels, cut at a reduced rate, growth in the absence" and should read --tide T parallels, but at a reduced rate, growth in the absence--

Column 16, line 33 reads "A for 8 days. Cultures ere pulsed and harvested daily and the" and should read --A for 8 days. Cultures were pulsed and harvested daily and the--

Column 16, line 39 reads "rubella vaccine: NMR), superantigens such as Staphylococ-" and should read --rubella vaccine: MMR), superantigens such as Staphylococ- --

Column 16, line 41 reads "(anti-CD3) pBMC will proliferate as indicated by a prolif-" and should read --(anti-CD3) PBMC will proliferate as indicated by a prolif- --

Column 18, line 34 reads "She was treated with LIORESEAL™ (baclofen) with some" and should read --She was treated with LIORESAL™ (baclofen) with some--

Column 22, line 4 reads "in presence of mitogen±Peptide T-cpm in absence of" and should read --in presence of mitogen±Peptide T ÷ cpm in absence of--

Column 22, line 17 Table III, fifth column heading reads "PHZ$^4$" and should read --PHA$^4$--

Column 22, lines 29-35 please delete second occurrence of footnotes of Table III.

Column 22, line 41 reads "PBMC (cpm of A=142±86, B=148±84) cocultured in 200µl" and should read --PBMC (cpm of A=142=86, B=148=84) cocultured in 200µl--

UNITED STATES PATENT AND TRADEMARK OFFICE
CERTIFICATE OF CORRECTION

PATENT NO. : 5,756,449

DATED : May 26, 1998

INVENTOR(S) : Anders Jorgen Andersen, et al.

It is certified that error appears in the above-identified patent and that said Letters Patent is hereby corrected as shown below:

Column 23, line 17 reads "assay. $p56^{lvck}$ is a CD4 associated tyrosine kinase involved" and should read --assay. $p56^{lck}$ is a CD4 associated tyrosine kinase involved--

Column 23, line 24 reads "inhibitory Tyr 505 (Abraham et al. *nature* 350 62-66 (1991);" and should read --inhibitory Tyr 505 (Abraham et al. *Nature* 350 62-66 (1991);

Column 26, line 16 reads "manifest as intense hyperaesthesia of the left hip and though" and should read --manifest as intense hyperaesthesia of the left hip and thigh--

Column 27, line 65 reads "chemical Co. (St. Louis, Mo. USA). Peptide T was synthe-" and should read --Chemical Co. (St. Louis, Mo. USA). Peptide T was synthe- --

Column 28, line 1 reads "alcohol as preservative and was stored at 4° C. Peptide T was" and should read --alcohol as a preservative and was stored at 4° C. Peptide T was--

Column 28, line 29 reads "A FI of 2 indicates that cells have grown to twice their" and should read --A PI of 2 indicates that cells have grown to twice their--

Column 28, line 36 reads "Peptide T ($10^{-9}$M) was added at t+0 and 24 hours. At the end" and should read --Peptide T ($10^{-9}$M) was added at t=0 and 24 hours. At the end--

Column 28, line 46 reads "of $p \leq 0.05$ was considered a significant difference" and should read --of $p \leq 0.05$ was considered a significant difference--

UNITED STATES PATENT AND TRADEMARK OFFICE
CERTIFICATE OF CORRECTION

PATENT NO. : 5,756,449
DATED : May 26, 1998
INVENTOR(S) : Anders Jorgen Andersen, et al.

It is certified that error appears in the above-identified patent and that said Letters Patent is hereby corrected as shown below:

Column 28, line 50 reads "Peptide T ($1 \times 10^{-5}$M) added concurrently with mitogens (Day 1) or on" and should read --Peptide T ($1 \times 10^{-9}$M) added concurrently with mitogens (Day 1) or on--

Column 29, line 54 reads "eration signals by ligating MO/AMC and t cells via carbo-" and should read --eration signals by ligating MO/MAC and t cells via carbo- --

Column 30, line 30 reads "Molt-4 is a human T lymphoma cell line, $p56^{lock}$ negative," and should read --Molt-4 is a human T lymphoma cell line, $p56^{lck}$ negative, Column 30, line 31 reads "and Jurkat is a human T cell line, $p56^{lock}$ positive, that will" and should read --and Jurkat is a human T cell line, $p56^{lck}$ positive, that will--

Column 31, line 23 reads "enzymes and tumour necrosis factor alipha (TNF)." and should read --enzymes and tumour necrosis factor alpha (TNF).--

Column 31, line 49 reads "NO/MAC activation as indicated by enhanced levels of" and should read --MO/MAC activation as indicated by enhanced levels of--

Column 31, 55 reads "lipopolysaccharide (LPS) which initiate at leat four distinct" and should read --lipopolysaccharide (LPS) which initiate at least four distinct--

Column 31, line 62 reads "release grater amounts of TNF than those from normal" and should read --release greater amounts of TNF than those from normal--

Column 36, line 21 reads "37° the presence or absence of Peptide T. Tissue factor" and should read --37° in the presence or absence of Peptide T. Tissue factor--

UNITED STATES PATENT AND TRADEMARK OFFICE
CERTIFICATE OF CORRECTION

PATENT NO. : 5,756,449
DATED : May 26, 1998
INVENTOR(S) : Anders Jorgen Andersen, et al.

It is certified that error appears in the above-identified patent and that said Letters Patent is hereby corrected as shown below:

Column 36, line 54 reads "129-1367 (1992), Ware et al., "conceptualization and Mea-" and should read --129-137 (1992), Ware et al., "Conceptualization and Mea- --

Column 36, line 56 reads "Survey, Vol III; Mental Health", Rand Corporation 1979," and should read --Survey, Vol III: Mental Health", Rand Corporation 1979,--

Column 36, line 57 reads "and We et al., *Medical Care* 29(8) 786-98 (1991)." and should read --and Wu et al., *Medical Care* 29(8) 786-98 (1991).--

Column 37, line 33 reads "In the MS-modified MOS_HIV, either a trend or statisti-" and should read --In the MS-modified MOS-HIV, either a trend or statisti- --

Column 45, line 40, Claim 2 reads "wherein one or more amino acid(s), is/are deletered from" and should read --wherein one or more amino acid(s), is/are deleted from--

Signed and Sealed this

Twenty-seventh Day of July, 1999

Attest:

Q. TODD DICKINSON

*Attesting Officer*     *Acting Commissioner of Patents and Trademarks*

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: both ( i i ) MOLECULE TYPE: peptide ( i x ) FEATURE:
        ( A ) NAME/KEY: Peptide
        ( B ) LOCATION: 1..8
        ( D ) OTHER INFORMATION: /note= "Where Xaa 1 is Ala, Gly, Ser, Thr or absent"

( i x ) FEATURE:
    ( A ) NAME/KEY: Peptide
    ( B ) LOCATION: 1..8
    ( D ) OTHER INFORMATION: /note= "where Xaa 2 is Ala, Gly,
            Val, Ser, Thr or absent"

( i x ) FEATURE:
    ( A ) NAME/KEY: Peptide
    ( B ) LOCATION: 1..8
    ( D ) OTHER INFORMATION: /note= "where Xaa 3 is Ser, Thr or
            absent"

( i x ) FEATURE:
    ( A ) NAME/KEY: Peptide
    ( B ) LOCATION: 1..8
    ( D ) OTHER INFORMATION: /note= "where Xaa 4 is Ser, Thr,
            Asn, Glu, Arg, Ile, Leu or absent"

( i x ) FEATURE:
    ( A ) NAME/KEY: Peptide
    ( B ) LOCATION: 1..8
    ( D ) OTHER INFORMATION: /note= "where Xaa 5 is Ser, Thr,
            Asp or absent"

( i x ) FEATURE:
    ( A ) NAME/KEY: Peptide
    ( B ) LOCATION: 1..8
    ( D ) OTHER INFORMATION: /note= "where Xaa 6 is Thr, Ser,
            Asn, Arg, Gln, Lys, Trp or absent"

( i x ) FEATURE:
    ( A ) NAME/KEY: Peptide
    ( B ) LOCATION: 1..8
    ( D ) OTHER INFORMATION: /note= "where Xaa 7 is Tyr or
            absent"

( i x ) FEATURE:
    ( A ) NAME/KEY: Peptide
    ( B ) LOCATION: 1..8
    ( D ) OTHER INFORMATION: /note= "where Xaa 8 is Thr, Arg,
            Gly, Met, Met(o), Cys, Tyr, Gly or absent"

( i x ) FEATURE:
    ( A ) NAME/KEY: Peptide
    ( B ) LOCATION: 1..8
    ( D ) OTHER INFORMATION: /note= "where the ends may have CYS
            or are absent"

( x i ) SEQUENCE DESCRIPTION: SEQ ID NO:1:

Xaa Xaa Xaa Xaa Xaa Xaa Xaa Xaa
1               5

( 2 ) INFORMATION FOR SEQ ID NO:2:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: both ( i i ) MOLECULE TYPE: peptide ( i x ) FEATURE:
        ( A ) NAME/KEY: Peptide
        ( B ) LOCATION: 1..8
        ( D ) OTHER INFORMATION: /note= "where Xaa 1 is Ala, D-Ala;
            and Xaa 8 is Thr or Thr-amide"

( x i ) SEQUENCE DESCRIPTION: SEQ ID NO:2:

Xaa Ser Thr Thr Thr Asn Tyr Xaa
1               5

( 2 ) INFORMATION FOR SEQ ID NO:3:

-continued (i) SEQUENCE CHARACTERISTICS:
    (A) LENGTH: 8 amino acids
    (B) TYPE: amino acid
    (C) STRANDEDNESS: single
    (D) TOPOLOGY: both (ii) MOLECULE TYPE: peptide (ix) FEATURE:
    (A) NAME/KEY: Peptide
    (B) LOCATION: 1..8
    (D) OTHER INFORMATION: /note= "Ala 1 is D-Ala"

(xi) SEQUENCE DESCRIPTION: SEQ ID NO:3:

```
Ala  Ser  Thr  Thr  Thr  Asn  Tyr  Thr
1                   5
```

(2) INFORMATION FOR SEQ ID NO:4:

(i) SEQUENCE CHARACTERISTICS:
    (A) LENGTH: 5 amino acids
    (B) TYPE: amino acid
    (C) STRANDEDNESS: single
    (D) TOPOLOGY: both (ii) MOLECULE TYPE: peptide (ix) FEATURE:
    (A) NAME/KEY: Peptide
    (B) LOCATION: 1..5
    (D) OTHER INFORMATION: /note= "core"

(xi) SEQUENCE DESCRIPTION: SEQ ID NO:4:

```
Thr  Thr  Asn  Tyr  Thr
1                   5
```

(2) INFORMATION FOR SEQ ID NO:5:

(i) SEQUENCE CHARACTERISTICS:
    (A) LENGTH: 8 amino acids
    (B) TYPE: amino acid
    (C) STRANDEDNESS: Not Relevant
    (D) TOPOLOGY: circular (ii) MOLECULE TYPE: peptide (xi) SEQUENCE DESCRIPTION: SEQ ID NO:5:

```
Ala  Ser  Thr  Thr  Thr  Asn  Tyr  Thr
1                   5
```

(2) INFORMATION FOR SEQ ID NO:6:

(i) SEQUENCE CHARACTERISTICS:
    (A) LENGTH: 8 amino acids
    (B) TYPE: amino acid
    (C) STRANDEDNESS: Not Relevant
    (D) TOPOLOGY: both (ii) MOLECULE TYPE: peptide (ix) FEATURE:
    (A) NAME/KEY: Peptide
    (B) LOCATION: 1..8
    (D) OTHER INFORMATION: /note= "aa1 is D-Alanine"

(xi) SEQUENCE DESCRIPTION: SEQ ID NO:6:

```
Ala  Ala  Ser  Ser  Ser  Asn  Tyr  Met
1                   5
```

(2) INFORMATION FOR SEQ ID NO:7:

(i) SEQUENCE CHARACTERISTICS:

(A) LENGTH: 5 amino acids
(B) TYPE: amino acid
(C) STRANDEDNESS: Not Relevant
(D) TOPOLOGY: both (ii) MOLECULE TYPE: peptide (xi) SEQUENCE DESCRIPTION: SEQ ID NO:7:

Thr Asp Asn Tyr Thr
1               5

(2) INFORMATION FOR SEQ ID NO:8:

(i) SEQUENCE CHARACTERISTICS:
(A) LENGTH: 5 amino acids
(B) TYPE: amino acid
(C) STRANDEDNESS: Not Relevant
(D) TOPOLOGY: both (ii) MOLECULE TYPE: peptide (xi) SEQUENCE DESCRIPTION: SEQ ID NO:8:

Thr Thr Ser Tyr Thr
1               5

(2) INFORMATION FOR SEQ ID NO:9:

(i) SEQUENCE CHARACTERISTICS:
(A) LENGTH: 4 amino acids
(B) TYPE: amino acid
(C) STRANDEDNESS: Not Relevant
(D) TOPOLOGY: both (ii) MOLECULE TYPE: peptide (ix) FEATURE:
(A) NAME/KEY: Peptide
(B) LOCATION: 1..4
(D) OTHER INFORMATION: /note= "aa1 is D-Thr, aa4 is D-Thr"

(xi) SEQUENCE DESCRIPTION: SEQ ID NO:9:

Thr Thr Tyr Thr
1

(2) INFORMATION FOR SEQ ID NO:10:

(i) SEQUENCE CHARACTERISTICS:
(A) LENGTH: 8 amino acids
(B) TYPE: amino acid
(C) STRANDEDNESS: Not Relevant
(D) TOPOLOGY: both (ii) MOLECULE TYPE: peptide (ix) FEATURE:
(A) NAME/KEY: Peptide
(B) LOCATION: 1..8
(D) OTHER INFORMATION: /note= "aa1 is D-Ala, aa3 is D-Thr, aa5 is D-thr, aa8 is D-Thr"

(xi) SEQUENCE DESCRIPTION: SEQ ID NO:10:

Ala Ser Thr Thr Thr Asn Tyr Thr
1               5

(2) INFORMATION FOR SEQ ID NO:11:

(i) SEQUENCE CHARACTERISTICS:
(A) LENGTH: 8 amino acids
(B) TYPE: amino acid
(C) STRANDEDNESS: Not Relevant
(D) TOPOLOGY: both

```
( i i ) MOLECULE TYPE: peptide ( i x ) FEATURE:
        ( A ) NAME/KEY: Peptide
        ( B ) LOCATION: 1..8
        ( D ) OTHER INFORMATION: /note= "aa1 is D-Ser, aa3 is D-Thr,
              aa5 is D- Thr, aa8 is D-Thr"

( x i ) SEQUENCE DESCRIPTION: SEQ ID NO:11:

Ser  Ser  Thr  Thr  Thr  Thr  Tyr  Thr
1                    5
```